(12) United States Patent
Hibri

(10) Patent No.: US 11,076,973 B2
(45) Date of Patent: Aug. 3, 2021

(54) INTRAGASTRIC HELICAL PROSTHESIS FOR TREATING OBESITY

(71) Applicant: Nadi Hibri, San Antonio, TX (US)

(72) Inventor: Nadi Hibri, San Antonio, TX (US)

(73) Assignee: SPICA MEDICAL TECHNOLOGIES LLC, San Antonio, TX (US)

( * ) Notice: Subject to any disclaimer, the term of this patent is extended or adjusted under 35 U.S.C. 154(b) by 160 days.

(21) Appl. No.: 16/379,387

(22) Filed: Apr. 9, 2019

(65) Prior Publication Data
US 2019/0307592 A1   Oct. 10, 2019

Related U.S. Application Data

(60) Provisional application No. 62/655,331, filed on Apr. 10, 2018.

(51) Int. Cl.
*A61F 5/00* (2006.01)
*A61M 29/02* (2006.01)

(52) U.S. Cl.
CPC ............ *A61F 5/003* (2013.01); *A61F 5/0036* (2013.01); *A61F 5/0076* (2013.01); *A61M 29/02* (2013.01); *A61M 2210/1053* (2013.01)

(58) Field of Classification Search
CPC .... A61F 5/0013; A61F 5/0033; A61F 5/0073; A61F 5/004; A61F 5/0043; A61F 5/0003; A61F 5/003; A61F 5/0036; A61F 5/0076; A61F 5/0046; A61M 2210/1053; A61M 29/02
See application file for complete search history.

(56) References Cited

U.S. PATENT DOCUMENTS

| 2,402,666 | A | 6/1946 | Raspet | |
|---|---|---|---|---|
| 2,606,191 | A | 9/1952 | Foster | |
| 2006/0058834 | A1* | 3/2006 | Do | A61L 31/10 606/200 |
| 2007/0239284 | A1* | 10/2007 | Skerven | A61F 5/0003 623/23.65 |
| 2008/0109027 | A1* | 5/2008 | Chen | A61F 5/0036 606/191 |

(Continued)

OTHER PUBLICATIONS

Orberag®,*Non-Surgical Weight Loss Balloon System*, as available https://www.orbera.com/ on Feb. 16, 2021, 3 pages.

*Primary Examiner* — Katherine H Schwiker
*Assistant Examiner* — Raihan R Khandker
(74) *Attorney, Agent, or Firm* — Patterson Thuente Pedersen, PA

(57) ABSTRACT

A transorally implantable intragastric helical prosthesis for treating obesity. The helical prosthesis has a primary lumen having a balloon element therein, and a secondary lumen having a spring wire element therein. The prosthesis also includes an end fitting. When deployed into the stomach of a patient, the prosthesis spontaneously reverts from a linear pre-deployment configuration to a helical post-deployment configuration by the biasing action of the spring wire element. Upon inflation of the elongated balloon element, the prosthesis unwinds, dynamically engaging and stretching the stomach wall, reducing the intragastric space, and slowing down gastric emptying, thus promoting a feeling of satiety, which may result in weight loss.

28 Claims, 20 Drawing Sheets

(56) References Cited

U.S. PATENT DOCUMENTS

| | | | |
|---|---|---|---|
| 2009/0247933 A1* | 10/2009 | Maor | A61B 18/14 604/20 |
| 2011/0071553 A1* | 3/2011 | Dlugos, Jr. | A61F 2/0036 606/151 |
| 2011/0270022 A1* | 11/2011 | Honaryar | A61F 5/0059 600/37 |
| 2012/0095497 A1* | 4/2012 | Babkes | A61F 5/0036 606/192 |
| 2013/0253417 A1* | 9/2013 | Dinh | A61M 25/0053 604/28 |
| 2014/0025031 A1* | 1/2014 | Lam | A61F 5/0036 604/500 |
| 2014/0066896 A1* | 3/2014 | Tilson | A61M 25/1006 604/509 |
| 2014/0066968 A1 | 3/2014 | Pavlovic | |
| 2015/0174370 A1* | 6/2015 | Tsukashima | A61B 17/12113 604/890.1 |
| 2016/0095731 A1* | 4/2016 | Connor | A61F 5/0076 604/9 |
| 2018/0344989 A1* | 12/2018 | Laduca | A61M 25/0155 |

* cited by examiner

INTRAGASTRIC HELICAL PROSTHESIS FOR TREATING OBESITY

RELATED APPLICATION

The present application claims the benefit of U.S. Provisional Application No. 62/655,331 filed Apr. 10, 2018, which is hereby incorporated herein in its entirety by reference.

TECHNICAL FIELD

The present disclosure is directed to an intragastric device for the treatment of obesity and/or to promote weight loss, and in particular, to an inflatable helical prosthesis that can be inserted into the stomach and removed transorally under fluoroscopic guidance.

BACKGROUND

Obesity is a complex metabolic illness that is associated with several comorbid diseases. Globally, obesity has become a prevalent and significant health issue. Accordingly, the demand for a safe and more effective minimally invasive therapy for weight reduction and intervention is increasing rapidly.

Endoscopic bariatric therapy is generally a preferred alternative to pharmacological treatment for obesity and provides many advantages over conventional surgical procedures. There are several endoscopic treatments for obesity. Intragastric balloons are well known in the art and have been successfully used in weight reduction and relief of comorbid disease symptoms. Such devices are generally placed in a patient's stomach through the mouth in an empty or deflated state, and thereafter filled with a suitable fluid. The balloon occupies space in the stomach, thereby creating a feeling of satiety, restricting food intake, and resulting in weight loss. Intragastric balloons typically are implanted for a period of around six months. The usual means of removing a balloon is to deflate it by puncturing the balloon with a sharp instrument and removing it utilizing endoscopic instruments to retrieve the balloon from the stomach.

Conventional intragastric balloons used for weight loss in obese patients pose difficulties in ease of access to inflate or deflate the balloon endoscopically. Specifically, in-situ adjustment of fluid distention of intragastric balloons has been technically challenging because of the slippery nature of such spherical balloons in the stomach. Further, it is difficult for the operator to endoscopically identify the deflation valve, grab and stabilize the balloon, and safely puncture its valve for further inflation or deflation of the balloon while avoiding puncturing the balloon wall or injuring the patient.

Various balloon prostheses have been developed in the past to effect a feeling of satiety and restriction of food intake. For example, one conventional device is a stomach insert for treating obesity by reducing the stomach volume. Such an insert can comprise a flexible torus-shaped inflatable balloon having a central opening extending therethrough. At least a portion of the balloon can have a self-sealing feature to facilitate puncture thereof with a needle for inflating the balloon and sealing of the puncture upon removal of the needle. Yet another conventional device is an inflatable balloon with a number of wall portions that form a plurality of smooth-surfaced convex protrusions structured to permit engagement of the stomach wall by the balloon only at spaced localities, for minimizing mechanical trauma of the stomach wall by the balloon thus providing a limited surface area touching the gastric mucosa. The opening between the protrusions also allows an unobstructed pathway for the passage of food and gastric secretions to the small intestine.

Intragastric balloons of various types are made by several manufacturers. The ORBERA balloon manufactured by Apollo Endosurgery is an elastic silicone balloon filled with saline solution. The positioning assembly, which includes a balloon-filling tube and a catheter with the deflated balloon, is advanced to the gastro-esophageal junction. An endoscopic device is inserted to ensure the precise deployment of the intragastric balloon, which is then filled with methylene-mixed saline under direct-observation via the catheter. The ORBERA balloon is removed endoscopically by needle aspiration of the intragastric fluid and retrieved with a snare or grasper.

SUMMARY

It would be desirous to develop a therapeutically effective intragastric balloon with a simpler deployment and retrieval assembly. It could be advantageous for the balloon structure to include a system which is compatible with the dynamic environment and peristaltic waves of the stomach. Further, it could be desirous to provide an improved proximal end fitting coupled to a novel expandable helical assembly configured for weight loss in obese patients that may be accessed via a transoral catheter approach, under fluoroscopic guidance, to facilitate inflation-deflation regulation of a balloon assembly within the helical prosthesis in-situ.

The present disclosure relates, generally, to a transorally delivered intragastric helical prosthesis for the treatment of obesity. The prosthesis includes a helical assembly coupled to a proximal end fitting. The helical assembly is formed of an elongated flexible tubular body terminating distally in a soft terminal cap and a proximal end coupled to the proximal end fitting. The flexible tubular body includes a primary lumen having an unattached balloon element therein, and a secondary lumen having an unattached helical spring element therein.

In a first aspect, a helical assembly is provided with biasing means that spontaneously curves the prosthesis into a helical configuration, and thereafter, when an inflatable element therein is inflated, expand outwardly to a wider radius of curvature.

In an embodiment of the first aspect, the biasing means is a helical spring element constructed of a spring wire within a flexible tubing, the flexible tubing configured to maintain its cross-sectional shape during bending, and to remain substantially undistorted.

In another embodiment of the first aspect, the helical inflatable element is formed of an elongated balloon membrane having a helical or spiral configuration.

Upon deployment of the straightened, uninflated prosthesis from the lumen of an orogastric tube into the gastric cavity, the prosthesis automatically winds into a helical configuration by the biasing action of the spring wire. The helical prosthesis can be progressively and forcibly unwound by inflating the elongated balloon membrane, which enables the helical assembly to exert outward spring-like pressure along the internal stomach wall, providing the patient a feeling of satiety. Further, the expanded prosthesis reduces the intragastric space and slows down gastric emptying, diminishing food intake, thus leading to weight loss.

In a second aspect, a proximal end fitting for an expandable helical prosthesis includes a rigid housing for a front-facing access septum, a side-facing access septum, and a fluid reservoir in communication with the inflatable element of the helical assembly.

In an embodiment of the second aspect, the proximal end fitting is configured to provide secure mounting and attachment means to the support element and the inflatable element of the helical assembly.

In another embodiment of the second aspect, the housing of the proximal end fitting provides an external annular groove configured to engage a snare loop that fixes the fitting in secure position during inflation needle entry into the side-facing septum, to gain access to the fluid reservoir.

The above summary is not intended to describe each illustrated embodiment or every implementation of the subject matter hereof. The figures and the detailed description that follow more particularly exemplify various embodiments.

BRIEF DESCRIPTION OF THE DRAWINGS

The construction and advantages provided by embodiments of the disclosure will be more clearly understood from the following description of the various specific embodiments when read in conjunction with the accompanying drawings, in which.

Figure 1:
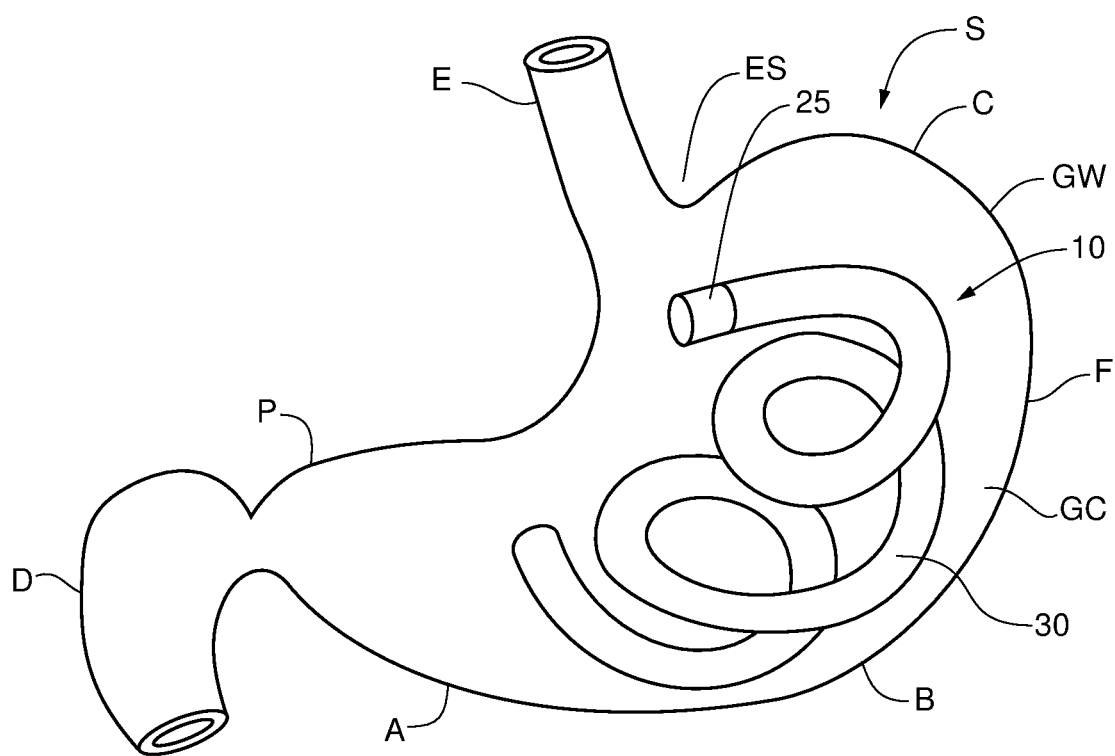
FIG. 1 is a schematic elevational view of a patient's stomach with a helical prosthesis in of the present disclosure in a reposed state.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION

The present disclosure is directed to embodiments of a transorally inserted intragastric device to treat obesity and/or for weight control, and related systems and methods. The mechanism of action of the intragastric device is based on unique expandable spring-like features. As the intragastric device expands and exerts outward pressure on the inner stomach wall, and responds dynamically to gastric peristalsis, the intragastric device induces early feelings of satiety. Furthermore, a central opening of the helical assembly of the intragastric device slows down gastric emptying, delaying the feeling of hunger between meals. Accordingly, a patient with the treatment device in his or her stomach may consume less food, thereby enabling him or her to lose weight. In addition, the helical configuration of the intragastric device permits the device to be straightened and stretched into a substantially linear delivery configuration, and allows for easy, safe, and rapid placement, adjustment, and removal.

FIG. 1 is a schematic representation of the anatomy of the human stomach with an exemplary helical prosthesis 10 therein. The stomach S temporarily stores food and releases it slowly into the duodenum D. The esophageal sphincter ES connects the lower esophagus E to the stomach S. Conventionally, the stomach portions are designated cardia C, fundus F, body B, and antrum A. The stomach wall is lined with muscle layers that undergo peristalsis. Towards the gastric outlet, the pylorus P acts as a sphincter, which restricts the free flow of food to the duodenum D, thus further contributing to the feeling of satiety.

Ingested food in the gastric cavity GC is subjected to a highly acidic environment (i.e., a pH of 1-2), and to digestive enzymes and salts. The inner stomach wall is lined with bicarbonate-secreting cells and mucous secreting cells that create a viscous physical barrier that protects the gastric wall.

With further reference to FIG. 1, an exemplary embodiment of helical prosthesis 10 is shown within the gastric cavity GC defined by a gastric wall GW of a patient undergoing treatment for obesity. In one embodiment, helical prosthesis 10 comprises a core element 50 defining a helical balloon element (shown in detail in the cross-sectional view of FIG. 4, and given reference number 40 therein), and a proximal end fitting 25. Unless otherwise stated herein, the proximal end of helical prosthesis 10 is the end nearer the esophageal sphincter ES, and the distal end of helical prosthesis 10 is the end nearer the antrum A, with respect to an intended orientation of helical prosthesis 10 in use (e.g., as depicted in FIG. 1). When helical prosthesis 10 is deployed into the gastric cavity GC, helical prosthesis 10 spontaneously and entropically reforms itself into a helical configuration in a reposed state due to intrinsic spring bias as will be discussed herein below.

Figure 2:
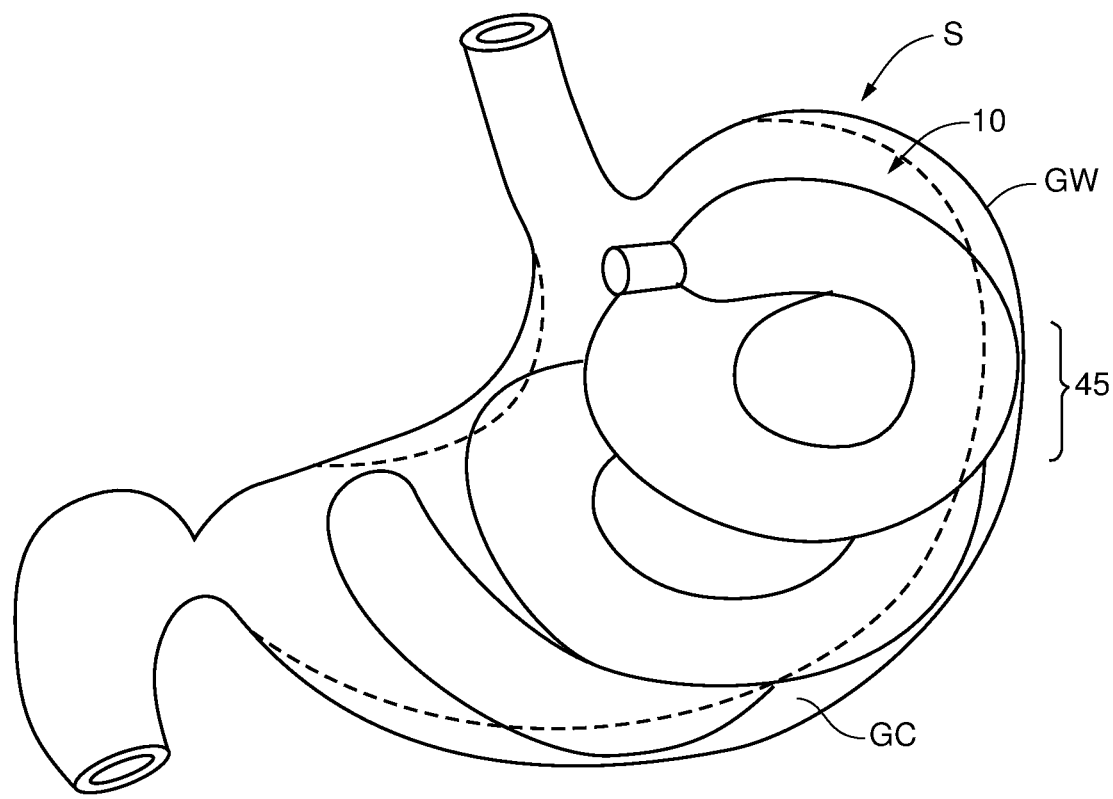
FIG. 2 depicts the helical prosthesis of FIG. 1 in an expanded state, with a dotted line demarcating the position of the stomach wall prior to expansion of the gastric cavity by the intragastric prosthesis and/or during peristalsis.

FIG. 2 depicts helical prosthesis 10 in an expanded state following inflation of helical balloon element 40 within core element 50 of helical prosthesis 10. As helical prosthesis 10 expands, helical prosthesis 10 also unwinds outwardly, stretching the gastric wall GW.

Figure 3:
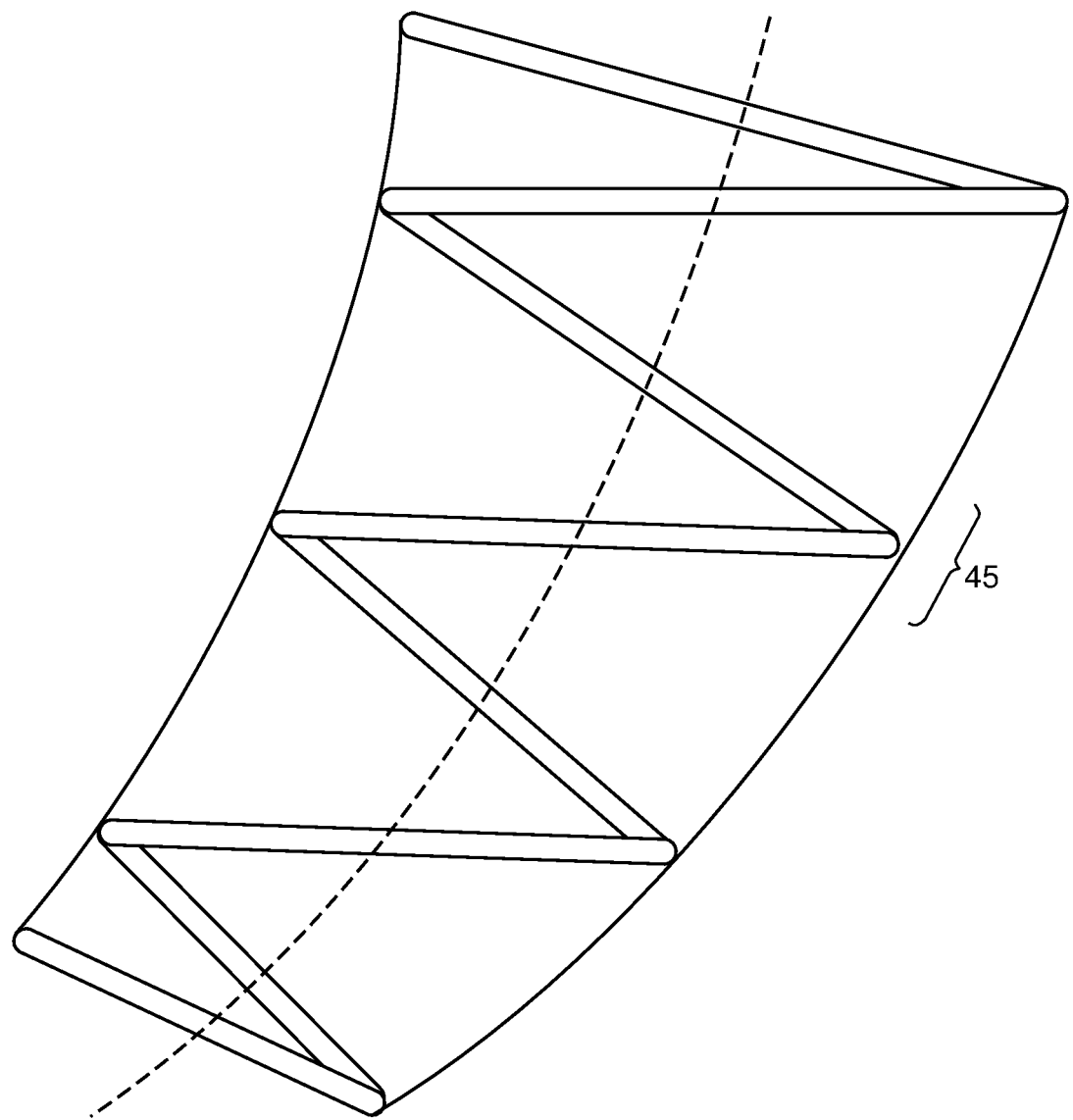
FIG. 3 is a schematic side view of another embodiment of a helical prosthesis having a progressive characteristic with convolutions of decreasing radii of curvature from proximal to distal, with a dotted line representing a curved central longitudinal axis substantially concentric with the curvature of the stomach.

Various embodiments of helical prosthesis 10 can be provided. For example, in an embodiment shown in FIG. 3, the number of helical convolutions of helical prosthesis 10 may be more or less than what is depicted in FIG. 1. In addition, the radii of curvature of the helical prosthesis 10 may vary. In one embodiment, the radius of curvature of a proximal convolution at the level of the gastric fundus F may be wide and progressively becomes smaller towards the pyloric region P of the stomach S. Furthermore, a longitudinal axis (represented by the dotted line in FIG. 3) extending along the central opening of the convolutions from a proximal end of helical prosthesis 10 to a distal end of helical prosthesis 10 may be curved, generally concentric with a central longitudinal axis of the stomach S.

Throughout this application, the term "expand" as used with reference to helical prosthesis 10 may, in relevant context, mean to: a) spread out, usually in every direction; b) dilate or increase in width or cross-sectional circumference; c) unwind incrementally in radius of curvature; d) elongate; e) adjust volume and space in the stomach over time; e) compress and/or extend due to the spring action of helical prosthesis 10; or f) some combination of any of a)-g).

Figure 4:
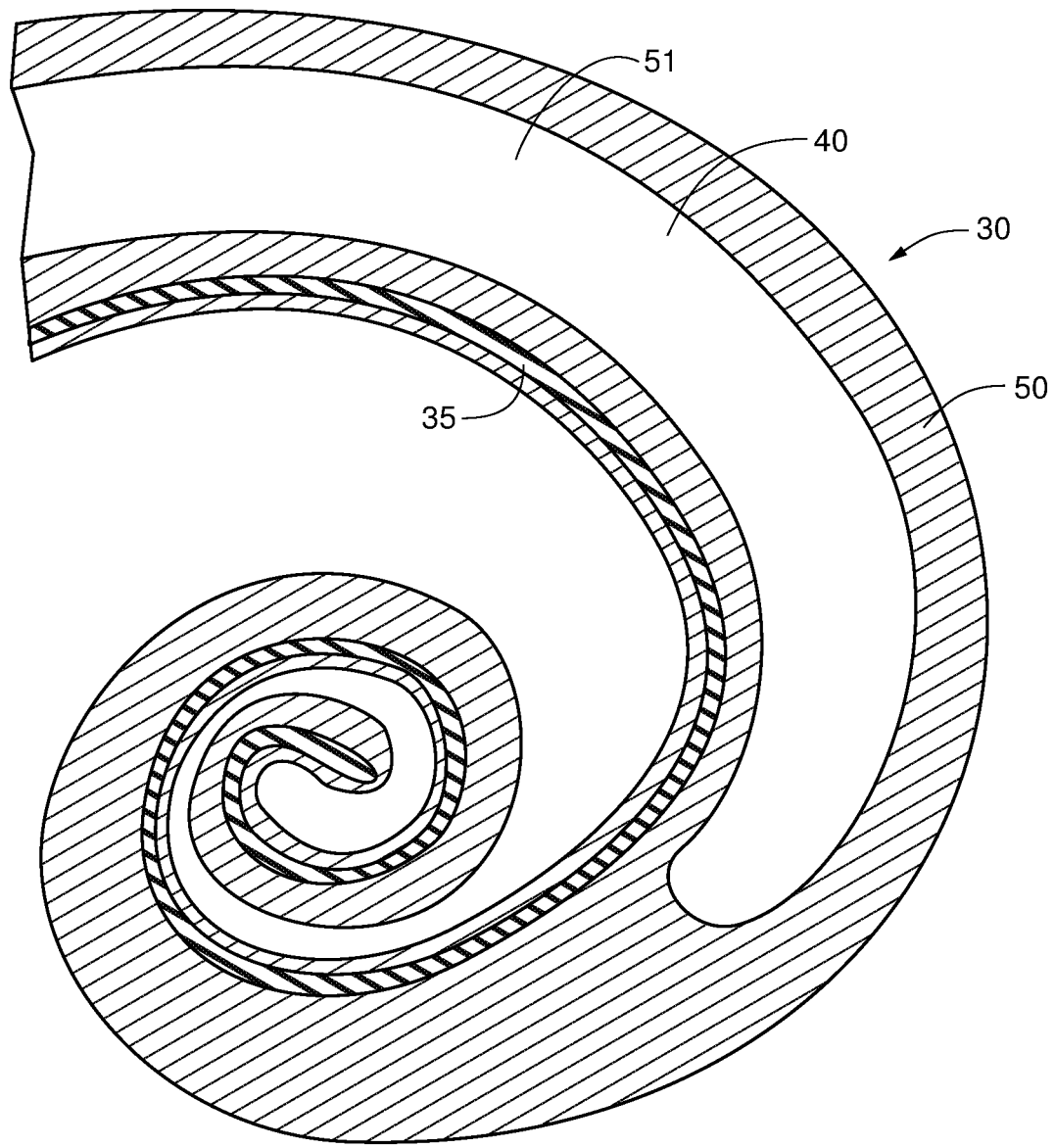
FIG. 4 is a cross-sectional view of a terminal segment of a helical intragastric prosthesis showing a pigtail configuration.

FIG. 4 shows a terminal (distal) segment of helical prosthesis 10 having a relatively tight coil, similar to that of a pigtail catheter used in interventional procedures, for example, as appreciated by those of ordinary skill in the art. However, in this particular application, the depicted segment can be configured to flex into an angle substantially orthogonal to the longitudinal axis of the rest of helical prosthesis 10. In use, the distal pigtail segment of helical prosthesis 10 lies in the gastric antrum A and guards against inadvertent expulsion of helical prosthesis 10 into the pylorus P. Additionally, the distal pigtail segment serves to further slow down emptying of the stomach contents, further contributing to a feeling of satiety.

Figure 5A:
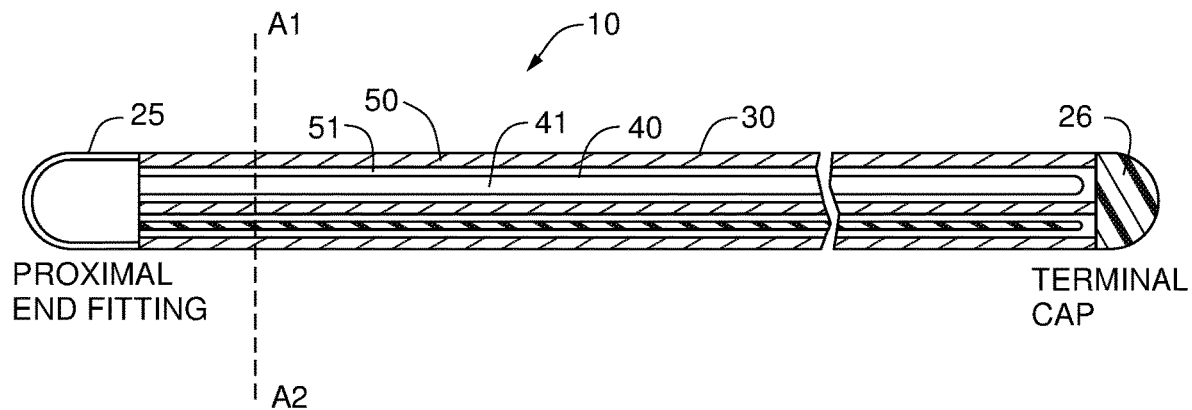
FIG. 5A is a cross-sectional view of a segment of a helical intragastric prosthesis that has been straightened in a deflated state.
Figure 5B:
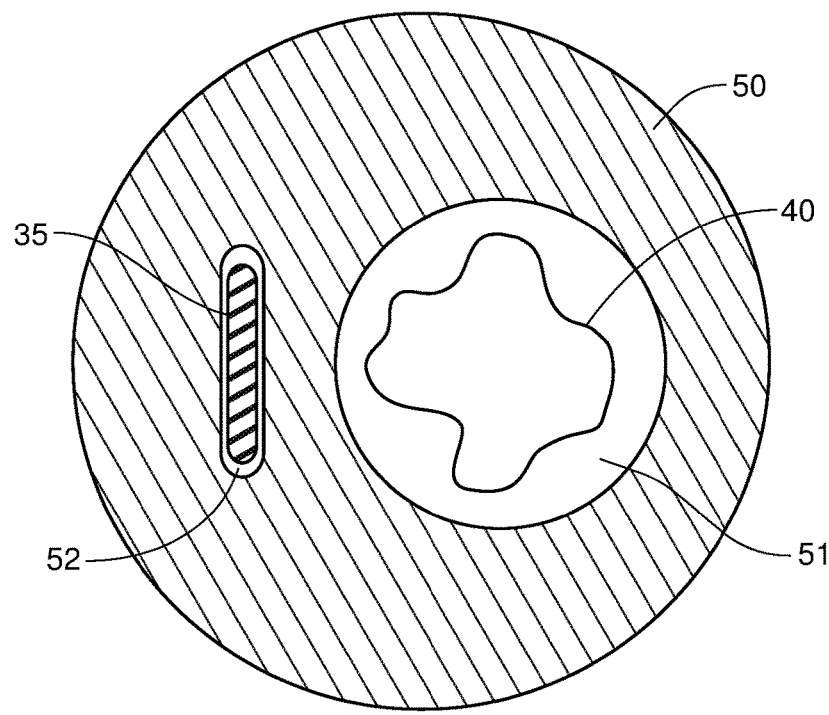
FIG. 5B is a cross-sectional view of the prosthesis shown in FIG. 5A taken along the line A1-A2.

FIGS. 5A and 5B depict a segment of helical prosthesis 10. As shown, helical prosthesis 10 is a flexible elongate structure comprising a soft core element 50 with an overlying surface element 60 (see FIGS. 13A, 13B and 14) and having lumens 51 and 52 extending therethrough. Lumen 51 surrounds or defines balloon 40. Helical spring element 35 is disposed within lumen 52. As can be seen in FIG. 5B in particular, the cross-section of helical prosthesis 10 is generally circular, with helical balloon element 40 being deflated and arranged loosely within primary lumen 51 of core element 50. Helical spring element 35 has a straight cross-curvature and is arranged loosely within secondary lumen 52.

In one embodiment, core element 50 is an elongated elastomeric tube having a proximal end coupled to proximal end fitting 25, and a distal end coupled to a soft polymeric terminal cap 26. Core element 50 has a primary lumen 51 with helical balloon element 40 extending therein and a secondary lumen 52 with helical spring element 35 extending therein. Helical balloon element 40 and helical spring element 35 can move freely within their respective lumens 51, 52 and are substantially unattached to core element 50.

Core element 50 can have a unitary silicone construction, though other materials may be used in other embodiments. For example, the silicone or other constituent material of core element 50 can be any suitable type of biocompatible silicone polymer or copolymer that can resist the high acidity atmosphere of the stomach. Although the present disclosure is directed principally to a silicone material, it is noted that silicon in some embodiments may be replaced with other types of biocompatible or implantable elastomers. Core element 50 may be fabricated by various molding techniques including, but not limited to, compression molding, injection molding, dip molding, extrusion, and lamination.

Various embodiments of core element 50 are envisioned. In one embodiment, core element 50 comprises a plurality of individual, generally ring-shaped elements, for example produced by co-extrusion form a continuous tubular structure. In another embodiment, a plurality of discrete, generally ring-shape polymeric bodies, which can possess differing durometers, are arranged in series and fused or bonded together to form the helical structure of core element 50. In another embodiment, core element 50 varies in cross-sectional configuration, diameter and flexibility in different convolutions of the helical structure. In one embodiment, core element 50 is substantially uniform in diameter and cross-sectional area along the length of helical prosthesis 10. In another embodiment, the cross-sectional configuration of core element 50 may be circular, oval, or ovoid.

Figure 8A:
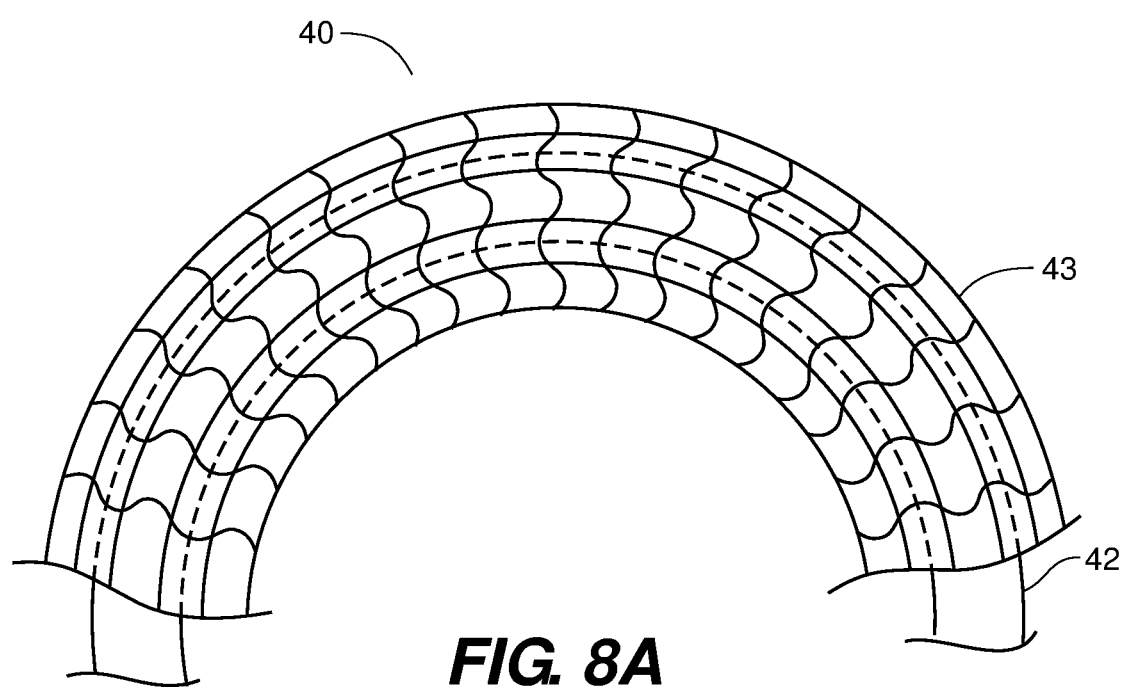
FIG. 8A is an enlarged perspective sectional view of a segment of a deflated balloon and schematic representation of a non-stretched fabric sleeve.

Referring to FIGS. 6A-6D, in this particular embodiment helical spring element 35 is disposed adjacent the lesser curved portion of the helical assembly 30 within lumen 52. In FIG. 8A, helical prosthesis 10 is in a reposed state, with helical balloon element 40 uninflated. Helical prosthesis 10 can be straightened and loaded into a delivery tube (shown in detail in FIGS. 16 and 17, and given reference number 21 therein), for delivery and deployment (discussed in more detail below), and when deployed into the gastric cavity GC helical prosthesis 10 spontaneously coils into a predetermined helical configuration due to an intrinsic memory determined by design and manufacturing parameters related primarily to helical spring element 35, and to a lesser extent helical balloon element 40, core element 50, and surface element 60.

Figure 6A:
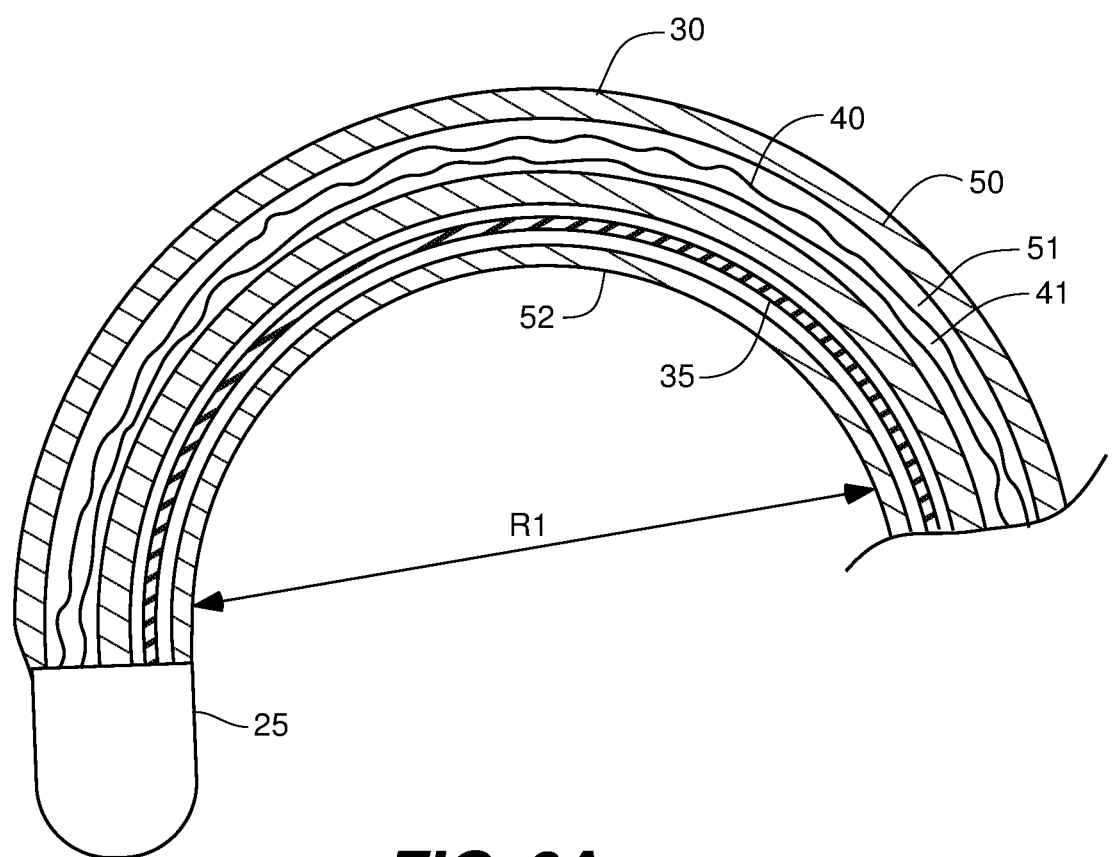
FIG. 6A is a cross-sectional view of a proximal segment of an intragastric helical prosthesis in a deflated reposed state showing winding of a segment secondary to a biasing action of a helical spring element.
Figure 6B:
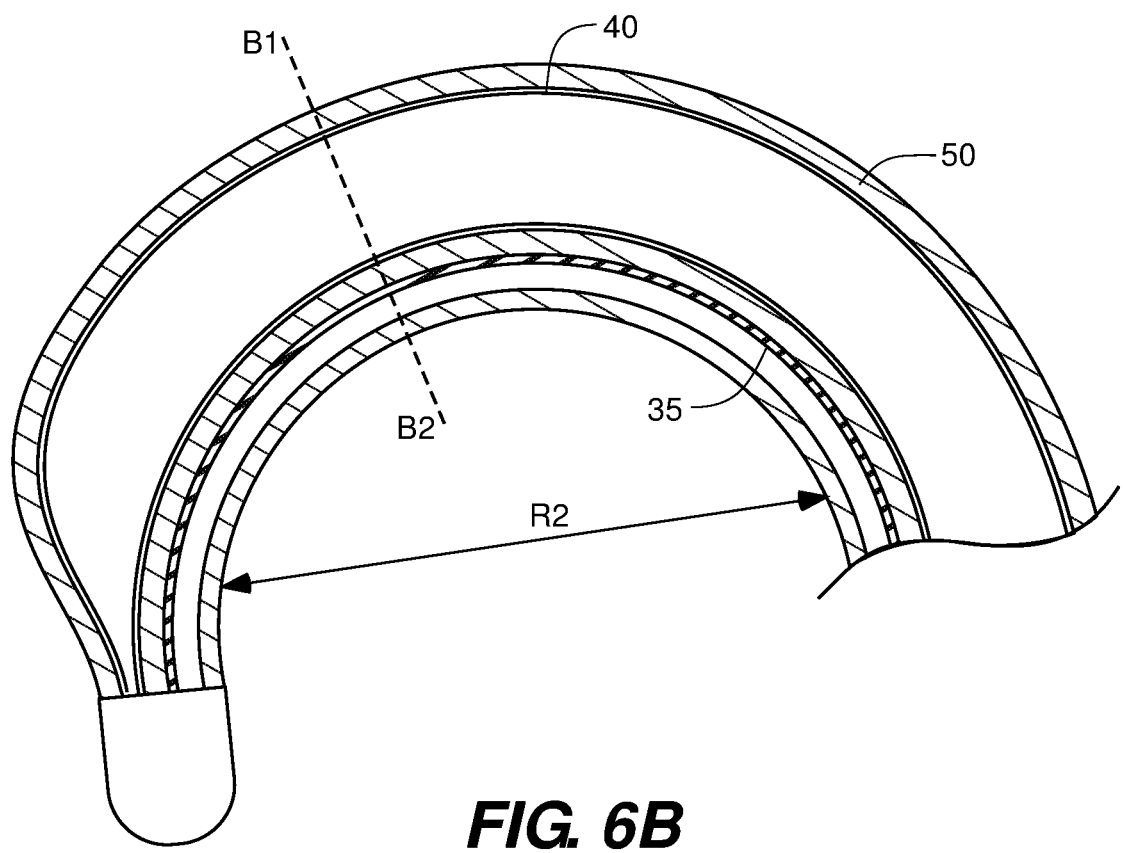
FIG. 6B is a cross-sectional view of the intragastric helical prosthesis of FIG. 6A following partial inflation of a helical balloon element and expansion of the helical assembly and illustrating an increase in the radius of curvature R2 compared to R1 in FIG. 6A.
Figure 6C:
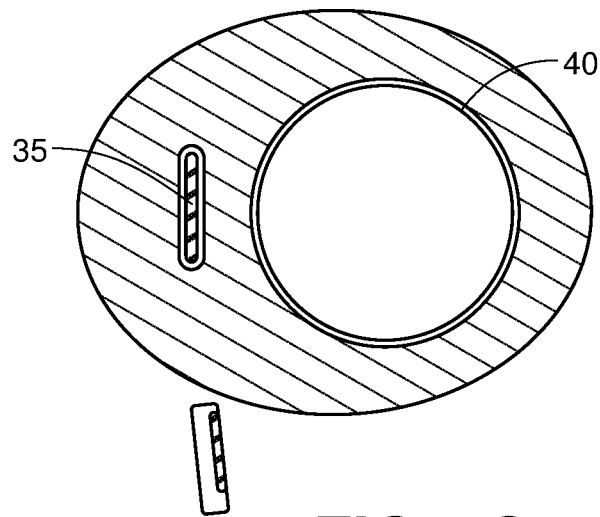
FIG. 6C is a cross-sectional view taken along the line B1-B2 of FIG. 6A showing a circular shape of the helical balloon element and a straight cross-curvature of the spring element.
Figure 6D:
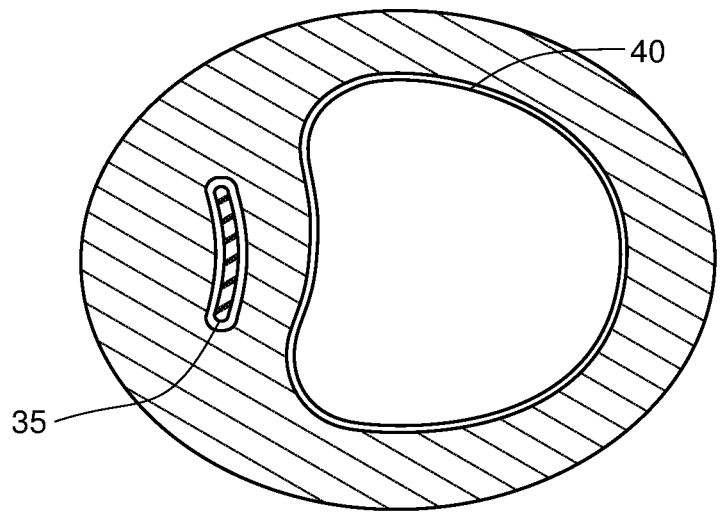
FIG. 6D is a cross-sectional view similar to FIG. 6C showing a bean shape of the helical balloon element and a curved cross-curvature of the spring element.

With reference to FIGS. 6A and 6B, as helical balloon element 40 is inflated, helical assembly 30 unwinds, increasing its radius of curvature from R1 (FIG. 6A) to R2 (FIG. 6B) and coming to substantially occupy primary lumen 51 of core element 50, thereby exerting an unwinding or straightening force on helical prosthesis 10. At the same time, helical spring element 35 is forcibly unwound and migrates outwardly within lumen 52, without jamming or locking against core element 50. Referring to FIG. 6C, helical spring element 35 is thrust outwardly against the wall of core element 50 and maintains its straight cross-curvature. The cross-section of core element 50 thereby is transformed from a generally circular configuration shown in FIG. 5B to a generally oval or ovoid configuration shown in FIG. 6C due to the asymmetrical expansion effect of helical balloon element 40 and the restraining effect of helical spring element 35. FIG. 6D is an alternative embodiment to FIG. 6C, whereby inflated helical balloon element 40 assumes a bean or kidney shape, and helical spring element 35 assumes a curved cross-curvature.

Figure 7A:
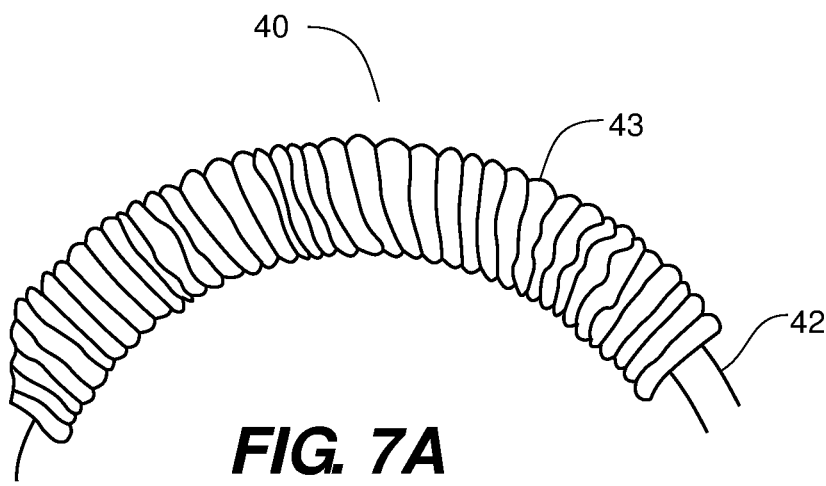
FIG. 7A is a top elevational view of a segment of a helical balloon element in a deflated state.
Figure 7B:
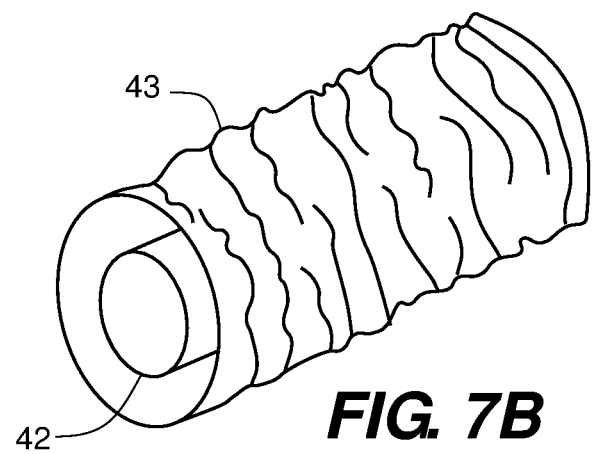
FIG. 7B is an enlarged perspective view of a segment of a helical balloon element similar to the one depicted in FIG. 7A and showing a deflated balloon and a non-stretched overlying fabric sleeve.
Figure 7C:
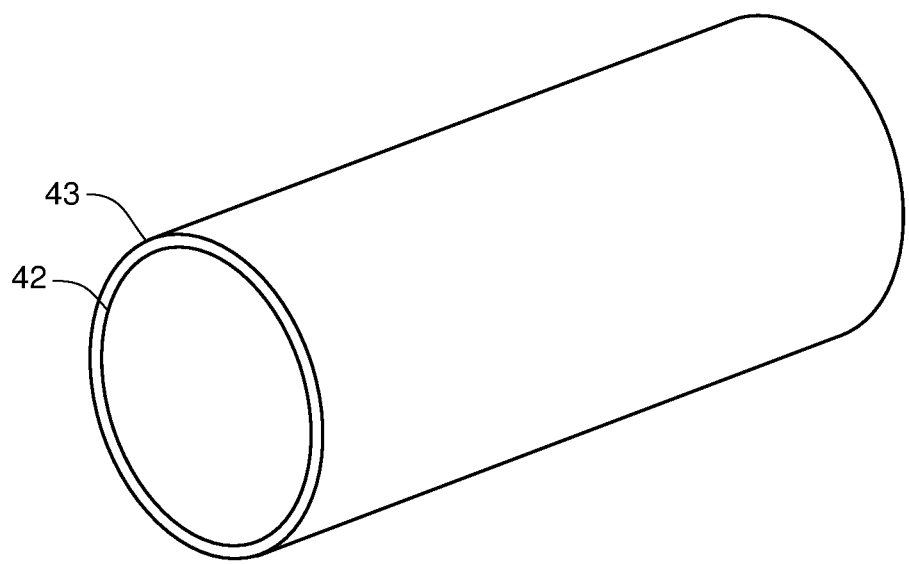
FIG. 7C depicts the segment of FIG. 7B following inflation of the balloon and stretching of the fabric sleeve.

Referring now to FIGS. 7A-7C, in some embodiments at least a portion of helical balloon element 40 comprises an elongate balloon membrane 42 and an overlying fiber matrix 43 arranged over balloon membrane 42. In one exemplary embodiment, fiber matrix 43 is unattached to balloon membrane 42 and is relatively movable in relation to a surface of balloon membrane 42. Inflation of balloon membrane 42 causes reconfiguration of the overlying fiber matrix 43 to urge the convolutions 45 (see FIG. 2) of helical prosthesis 10 to unwind and expand outwardly, thus exhibiting a degree of a straightening force at substantially low inflation pressures. Thus, helical prosthesis 10 is configured to effectively counteract the peristaltic pressure or peristaltic motility of a patient's stomach in a spring-like fashion. Additionally, in various embodiments the working length of balloon membrane 42 elongates up to about 10% during inflation, and the overlying fabric provides a curvature control mechanism that further facilitates curving of the balloon membrane.

Balloon membrane 42 comprises a compliant or semi-compliant material and may be molded straight or helically as needed. In one embodiment, when balloon membrane 42 is molded in a helical configuration out of a semi-compliant material, an overlying fiber matrix 43 may be omitted, and balloon membrane 42 alone can comprise helical balloon element 40.

When a compliant balloon membrane 42/fiber matrix 43 structure is used and as fluid inflation medium is introduced into balloon element 40, balloon membrane 42 is stretched, expanding radially and longitudinally and initially maintaining a molded balloon shape. When balloon membrane 42 is inflated further, it is constrained by fiber matrix 43 such that the folds or corrugations of fiber matrix 43 become biased towards unwinding helical prosthesis 10. This tendency of fiber matrix 43 to unwind and stretch balloon membrane 42 depends on the applied fluid pressure. Specifically, the pressurized inflation of balloon membrane 42 within fiber matrix 43 is characterized as a straightening force in the z plane of the helical axis, in addition to expansion in the horizontal and vertical planes. Fiber matrix 43 is unattached to balloon membrane 42, allowing the balloon membrane 42 to retain flexibility, which in turn enables balloon membrane 42 to expand at relatively low inflation pressure without kinking or buckling.

Balloons that are constructed from compliant materials are relatively more flexible than similar balloons constructed of semi-compliant or non-compliant material. However, compliant balloons may expand asymmetrically or overexpand and rupture when overinflated. Unlike the high-pressure, non-compliant balloons required in certain types of applications such as angioplasty and kyphoplasty, helical balloon element 40 implementation of the present disclosure does not require generation of a high force to initiate expansion or curving of helical prosthesis 10.

Thus, in accordance with one aspect of the disclosure balloon membrane 42 may comprise an elongated cylindrical balloon comprising a polymeric membrane having a nominal diameter between 5 mm and 10 mm, and a working pressure range that spans a nominal inflation pressure to a rated burst pressure, whereby the balloon exhibits about a 30% increase in mean straightening force when inflated across the working pressure range while helical prosthesis 10 is in a helical configuration. In one example, the working pressure is at least about 20 atmospheres.

Fiber matrix 43 may be formed from substantially inelastic material (e.g. Dacron, Nylon, Dyneema, Polyimide (PIM), and the like) shaped into fibers that are suitably flexible to be collapsed into a low-profile configuration when balloon membrane 42 is deflated. Longitudinal fibers and orthogonal fibers may be formed by the same or different strands of fiber or combination thereof. Fiber matrix 43 also can be formed with one single continuous fiber arranged both longitudinally and orthogonally.

Figure 8B:
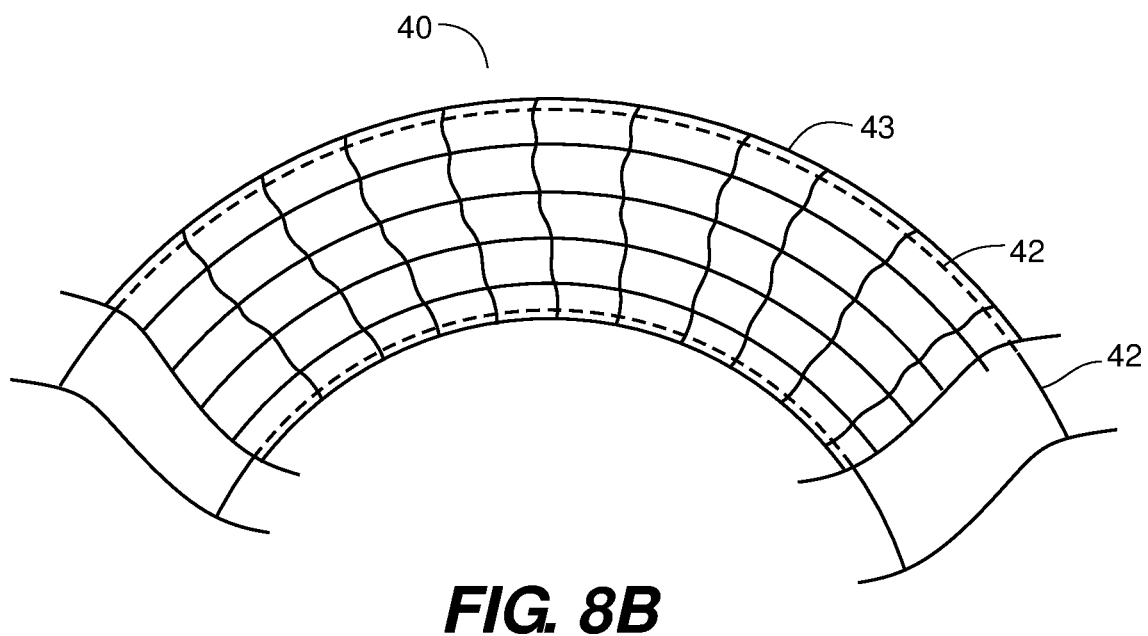
FIG. 8B depicts the segment of FIG. 8A following inflation of the balloon, stretching of the fabric sleeve, and increase in the radius of curvature of the segment of the helical balloon element.

Turning now to FIGS. 8A and 8B, in one embodiment, axially oriented fibers at the outer perimeter of fiber matrix 43 have a fiber density of about 20-30 fibers/inch and a fiber thickness of about 0.0005 inches to about 0.025 inches, and are relatively spaced apart. In this embodiment, the fiber density may increase progressively from the outer perimeter of fiber matrix 43 to the inner perimeter of fiber matrix 43. In other embodiments, the fiber compliance or elasticity increases from the outer perimeter of fiber matrix 43 to the inner perimeter of fiber matrix 43. The net effect of changing the fiber density and the fiber elasticity of fiber matrix 43 may be configured to differentially expand the matrix in a fashion intended to bias the balloon membrane towards unwinding of the helical prosthesis 10 upon balloon expansion. Fiber matrix 43 can comprise a knit fabric in one embodiment, whereby the prosthesis is sufficiently flexible that when deployed and inflated, the fabric permits bending of helical prosthesis 10 to conform to the size and curvature of the gastric wall GW in a particular patient.

FIGS. 9A, 9B, 10A, 10B, 11A, 11B, and 12 depict various embodiments of helical spring element 35. The embodiments of helical spring element 35 depicted in FIGS. 9A-9B and 10A-10B are uncovered helical springs of the type that wind or unwind upon elongation. Such springs can comprise metal or a polymer, for example. Various spring types are available or can be constructed to provide a wide range of features, namely, springs having a partially progressive characteristic, a positive gradient, a zero gradient, or a negative gradient. Further, it is possible to achieve a spring having a variable gradient, for example, including a plurality of positive, negative, and zero gradients. Advantageously, a helical spring that will exert a constant force at all times irrespective of the amount of deflection may be utilized in this application.

U.S. Pat. Nos. 2,402,666 and 2,609,191 disclose example springs that may be suitable for embodiments of helical prosthesis 10 and are incorporated herein by reference in their entireties.

Figure 9A:
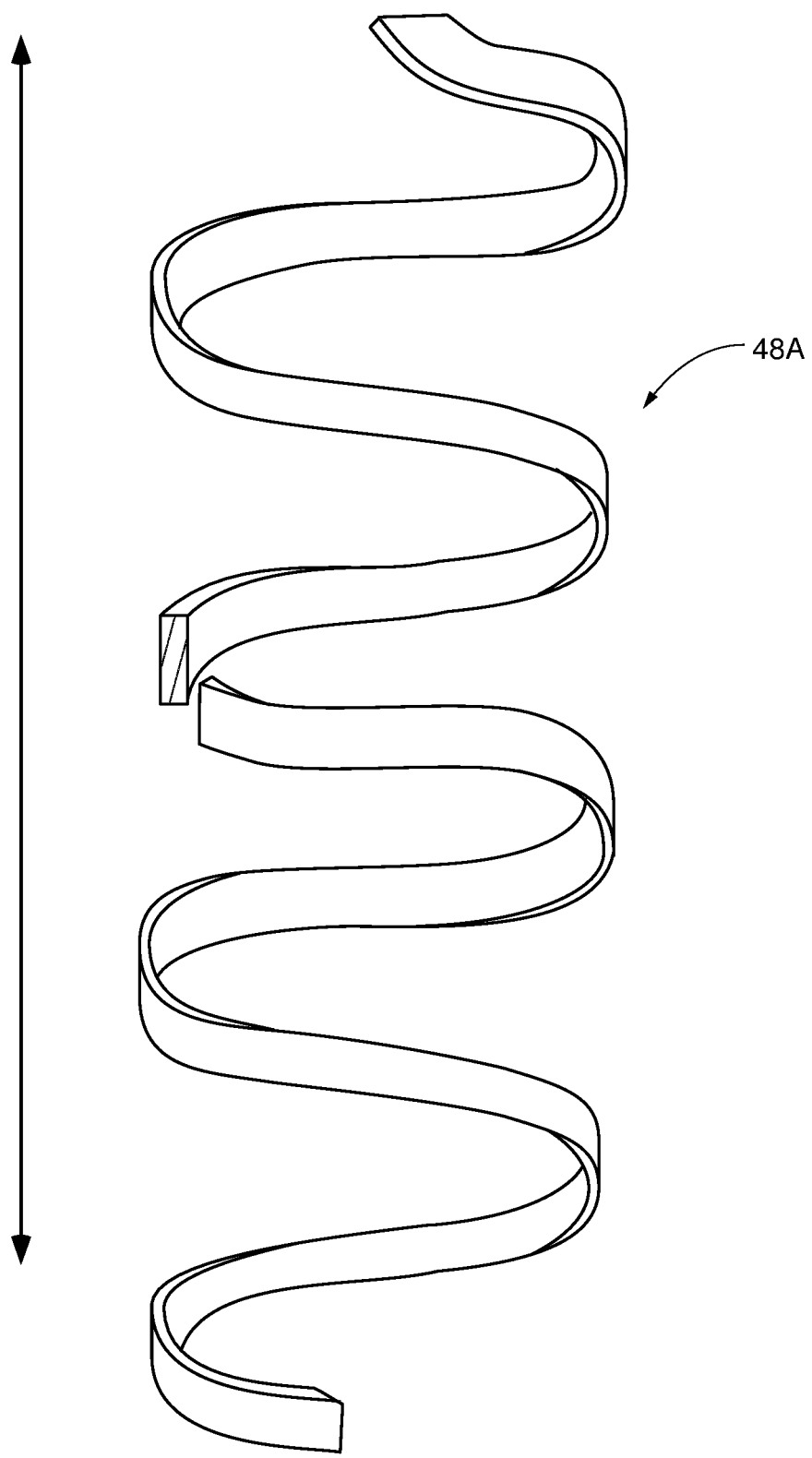
FIG. 9A is a front perspective view of an uncovered helical spring having a flat ribbon construction and wound with a greater cross-sectional dimension parallel to the axis of the helix.
Figure 9B:
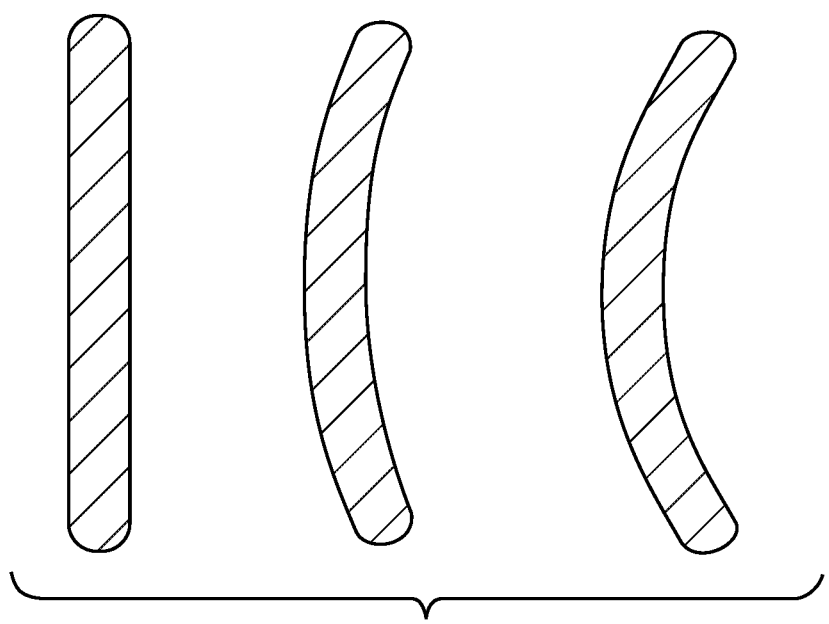
FIG. 9B depicts enlarged cross-sectional views of the helical spring shown of FIG. 9A with various degrees of cross-curvature.
Figure 10A:
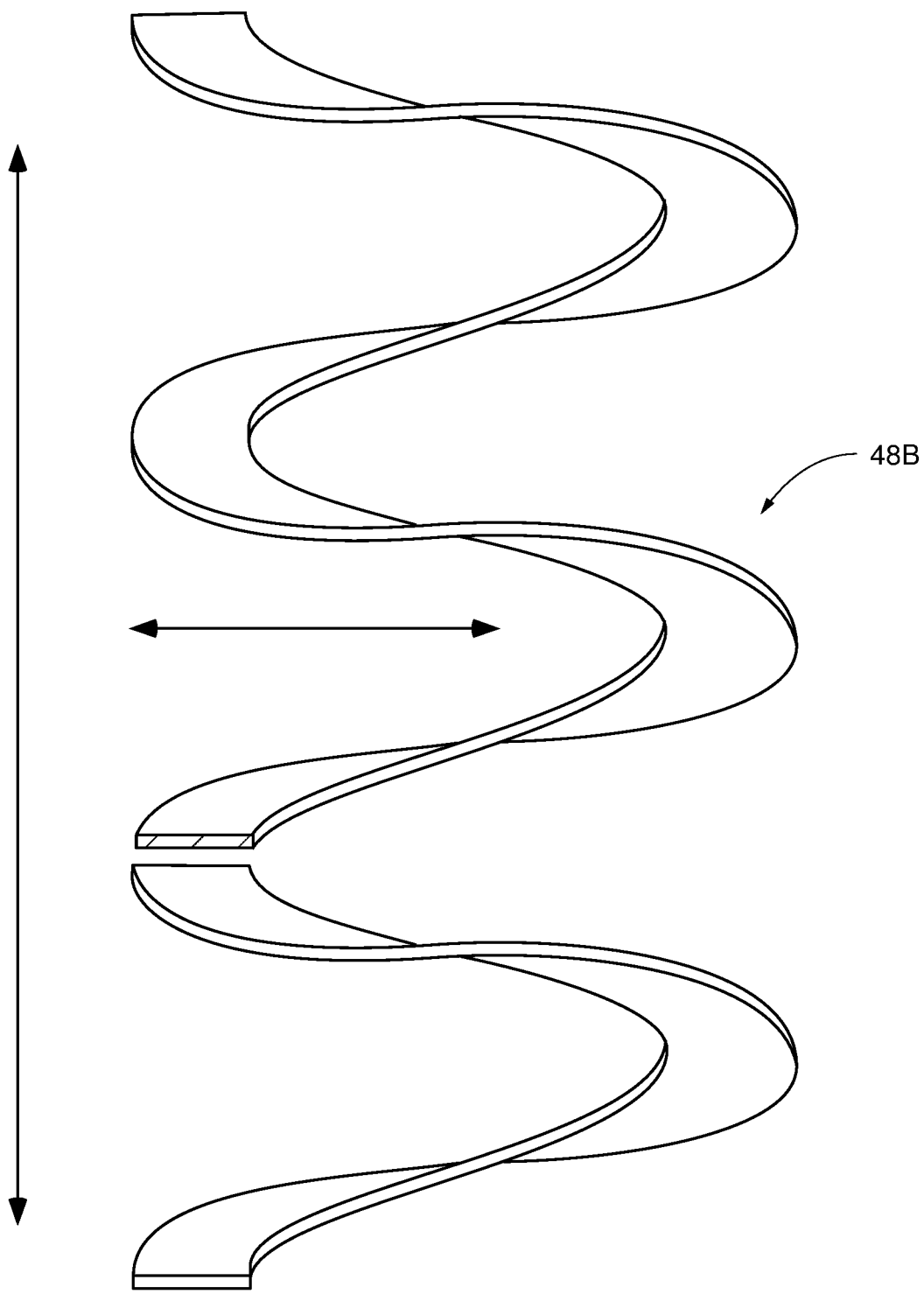
FIG. 10A depicts a helical spring formed of an elastic strip with its width parallel to the radii of the helix.
Figure 10B:
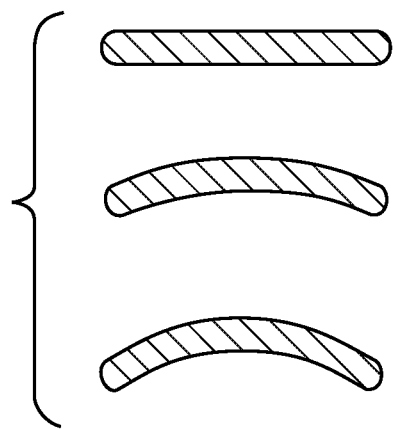
FIG. 10B depicts enlarged cross-sectional views of the elastic strip shown in FIG. 10A with various degrees of cross-curvature.

The example springs of FIGS. 9A-9B and 10A-10B are the type that wind or unwind upon elongation. The helical spring 48A shown in FIGS. 9A-9B is formed of an elastic strip having its width parallel to the axis of the helix. FIGS. 10A-10B are views similar to FIGS. 9A-9B but depict a spring 48B formed of an elastic strip with its width parallel to the radii of the helix.

Helical springs constructed of an elastic strip will wind or unwind when elongated according to the relative rigidity of the cross-section of the strip to bending as compared to the sections torsional rigidity. The tendency of such a spring to wind or unwind depends upon the relative torsional and bending rigidities of the strip, as well as on the pitch angle and the radius of the helix.

In FIG. 9A, spring 48A is a flat ribbon wound with its greater cross-sectional diameter parallel to the axis of the helix. This configuration of helical spring element 35 tends to unwind when elongated. On the other hand, if the spring 48B is wound as shown in FIG. 10A, helical spring element 35 is more rigid to torsion than to bending in its section and there consequently results a tendency for the spring to wind up.

In other embodiments, a coiled ribbon spring can comprise a tempered bend of uniform width and thickness and have a non-uniform set throughout its entire length. By using different amounts of cross-curvature, the spring can be rendered self-winding, self-extending, or balanced.

With respect to the radius of curvature of the increment forming the preceding convolution may be less than, equal to, or slightly larger than the next convolution.

When using coiled springs, such as coiled springs 48A and 48B, within lumen 52 of a soft elastomeric tubing such as core element 50, a challenge may arise in that the spring may translate to one side of lumen 52 and create friction and distortion that may result in locking or jamming of the spring. In order to eliminate or reduce the risk for such spring jamming, axially extending flexible tubing, similar to a vascular guiding catheter, can be arranged loosely at the circumference of spring 48A, 48B such that spring 48A, 48B can move tangentially during winding or unwinding of helical prosthesis 10. An embodiment including this flexible tubing is discussed in more detail below.

In view of the above-discussed risk, it can be advantageous to make coil spring 48A, 48B in a flattened form or in the form of a band, with the larger dimension of the material as seen in cross-section extending axially. It can be particularly advantageous in embodiments to design spring 48A, 48B with an essentially rectangular cross-section, as shown in the embodiments of FIGS. 9A-9B and 10A-10B.

With reference to spring 48A, 48B, a ribbon having cross-curvature imparts to the ribbon the tendency of an extended spring to rewind into its convoluted condition, and this can be increased or decreased a predetermined amount. In fact, by using different amounts of cross-curvature spring 48A, 48B can be rendered self-winding in that an extended portion of the ribbon will tend to wind on the coil, or it can be self-extending in that a coiled portion of the ribbon will tend to uncoil, or still it can be balanced in that the ribbon will remain unchanged from either extended or coiled conditions. By using a spring ribbon having a cross-curvature in this particular application, it is possible to retain the advantage of the aforementioned coiled spring in which the structural integrity, push-ability, and long term durability of the spring are maximized. By using various degrees of cross-curvature, in combination with the stresses inherent in this type of coiled spring, it is possible to minimize any tendency of the coiled ribbon, when unwound, to become entangled, or to assume a configuration other than that intended or programmed into the particular helical configuration.

A wire spring may be formed of a stressed ribbon which assumes a concave-convex cross-section in its reposed helical state. In this particular application, the concave side may be toward (or away from) the center of the helical axis.

The radius of curvature of the cross-section of the stressed ribbon may be varied by a forming process, which may be imparted to the ribbon either prior to the coiling operation, concurrently with the coiling operation, or subsequent to the coiling operation. It has been shown by testing that a coiled spring with a greater cross-sectional curvature would be somewhat weaker than a similar ribbon with a lesser cross-sectional curvature.

Conventionally, the stresses which tend to cause the helical spring ribbon to assume a tightly wound configuration have been called a longitudinal component and the force required to flatten the cross-curvature have been called the cross-component. For embodiments of helical prosthesis 10, a balance between the longitudinal component and the cross-component stresses of helical spring element 35 is desirable. The appropriate degree of stresses can be configured in order to maintain the structural integrity and resistance to entanglement of helical prosthesis 10 during deployment, and to offer sufficient resistance to the inward forces of gastric peristalsis, without being too rigid or stiff.

Figure 11A:
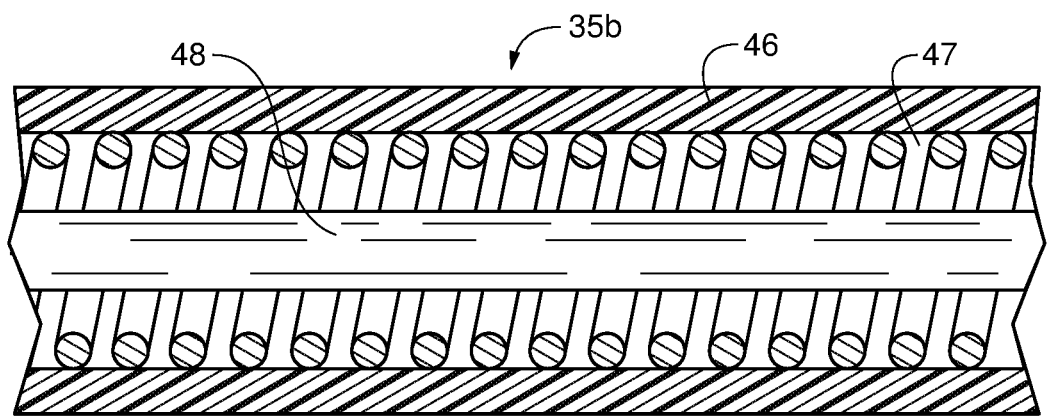
FIG. 11A is an enlarged view of a segment of an embodiment of a covered helical spring element shown in a straightened configuration.
Figure 11B:
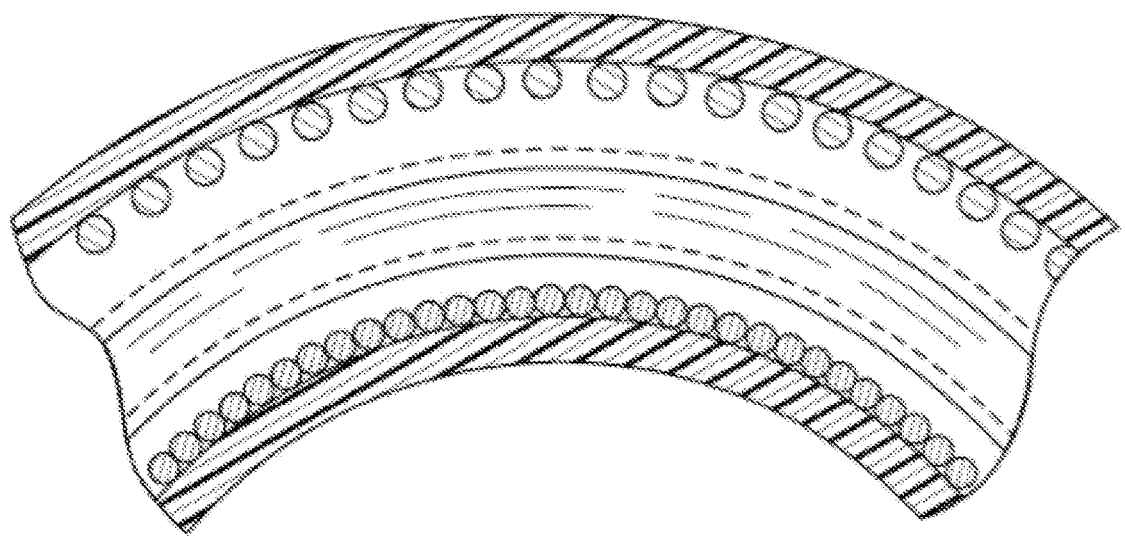
FIG. 11B depicts the segment of FIG. 11A in a curved configuration due to the intrinsic force of the helical spring wire therein.

With further reference to FIGS. 11A and 11B, in some embodiments the helical spring element 35 comprises a flexible tubing 46 defining a lumen 47 in which a spiral wire spring 48 is arranged. In one embodiment, spring 48 comprises a coil that is a flat ribbon stressed to assume a plurality of loosely wound convolutions when the coil is in a reposed state. By "loosely wound," it is meant that the coils are in a substantially separate relationship. Thus, the reposed radius of curvature of the increment of ribbon forms each convolution. In other embodiments, other windings or arrangements of the coils can be used.

Figure 12:
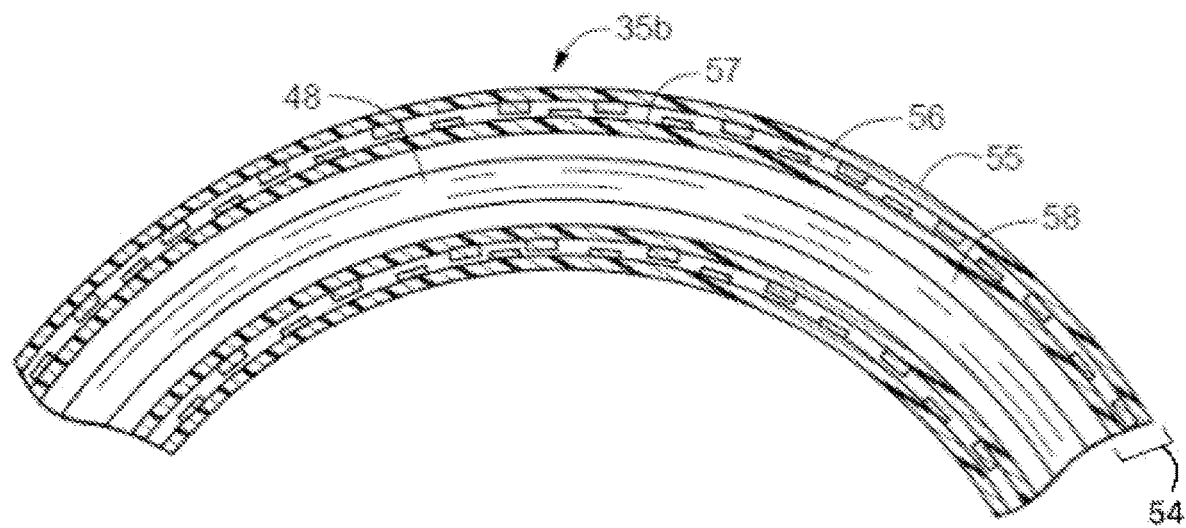
FIG. 12 is a view of another embodiment of a helical spring element with a different configuration of flexible tubing.

With reference to FIG. 12, an alternative embodiment of helical spring element 35 comprises a multi-layered flexible tubing 54 including an outer layer 55, an intermediate layer 56, and an inner layer 57 defining a lumen 58 in which is arranged a helical spring 48. Advantageously, lumen 58 may be ovoidal in cross-section to provide additional free space in lumen 58 to translate radially without becoming locked down upon bending. Furthermore, the presence of a reinforcement wire braid in intermediate layer 56 guards against deformation of the lumen upon bending of flexible tubing 54. Intermediate layer 56 comprises a support layer formed of a high tensile strength wire braid which has been tempered and hardened. Inner layer 57 defines lumen 58 and provides frictionless, resilient, and lubricious surface against spring 48. In one embodiment, inner layer 57 comprises PTFE membrane to insure a low friction surface against spring 48. In another embodiment, inner layer 57 incorporates or is coated with a lubricant. Outer layer 55 may include a thermoplastic polymer such as PEBAX available under the name ARNITEL. Outer layer 55 can have an inside diameter roughly corresponding to the outer diameter of intermediate layer 56, and a wall thickness of approximately 0.005 inches to 0.010 inches.

Figure 13A:
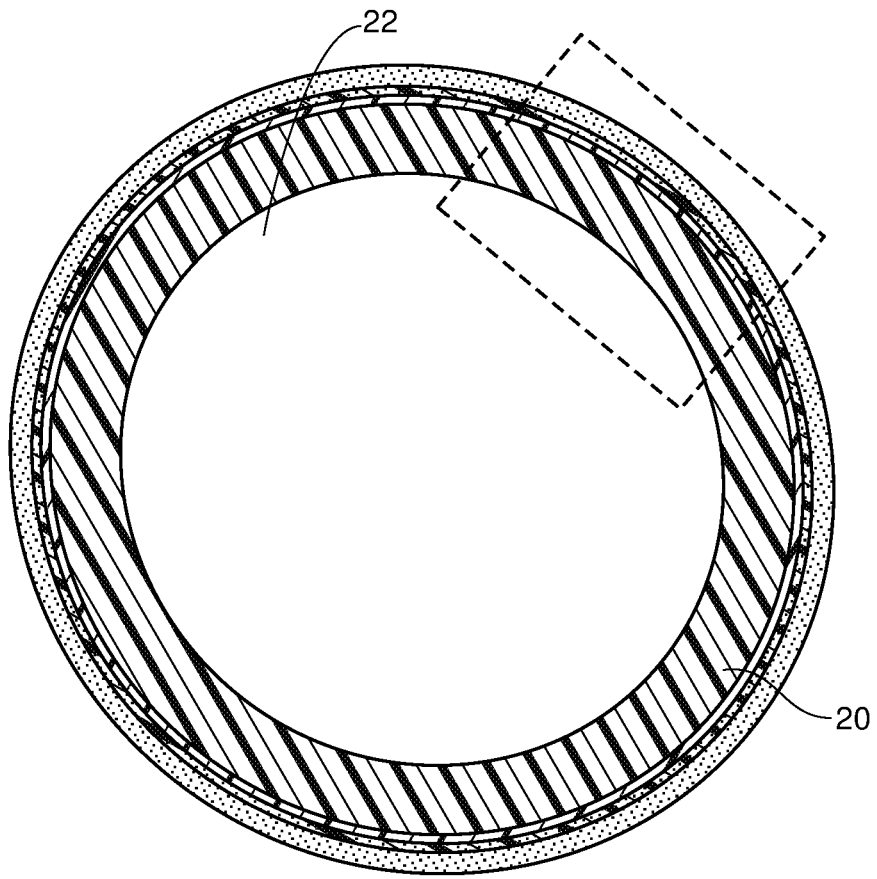
FIG. 13A is a cross-sectional view of an embodiment of a helical assembly including a core element.
Figure 13B:
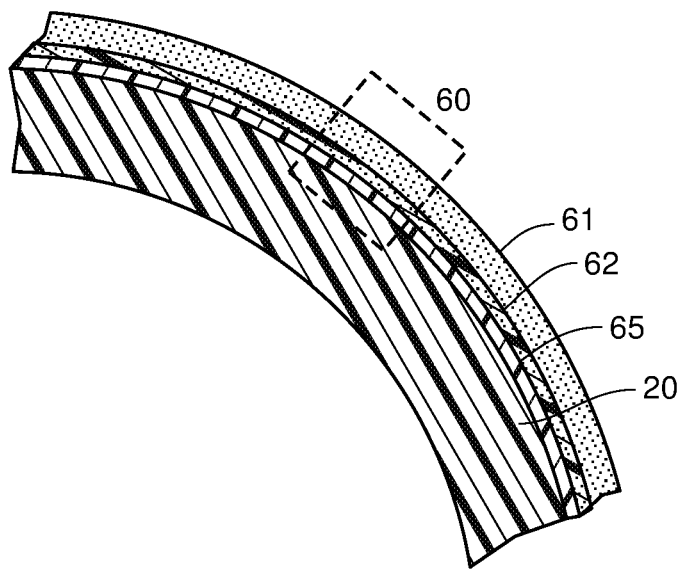
FIGS. 13B and 13C are enlarged views of the helical assembly of FIG. 13A.
Figure 13C:
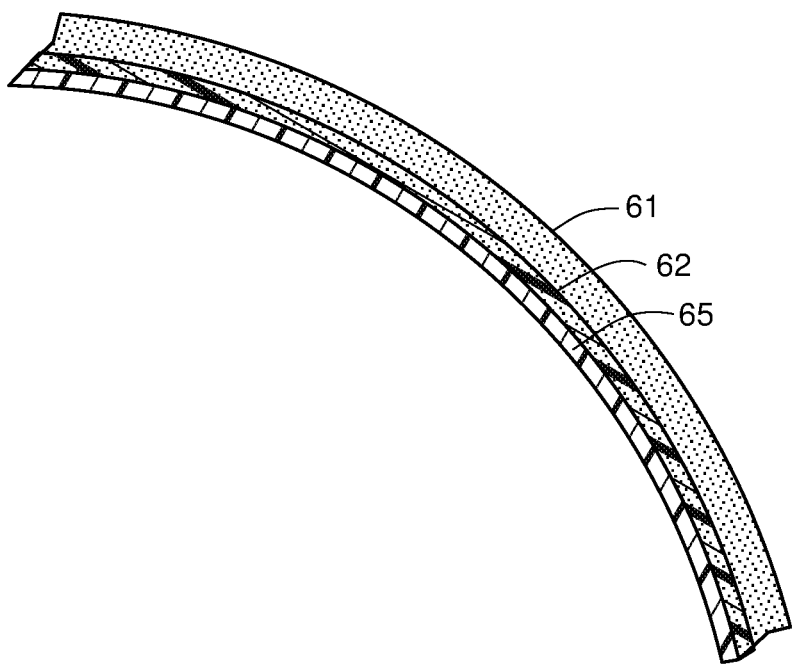
Figure 14:
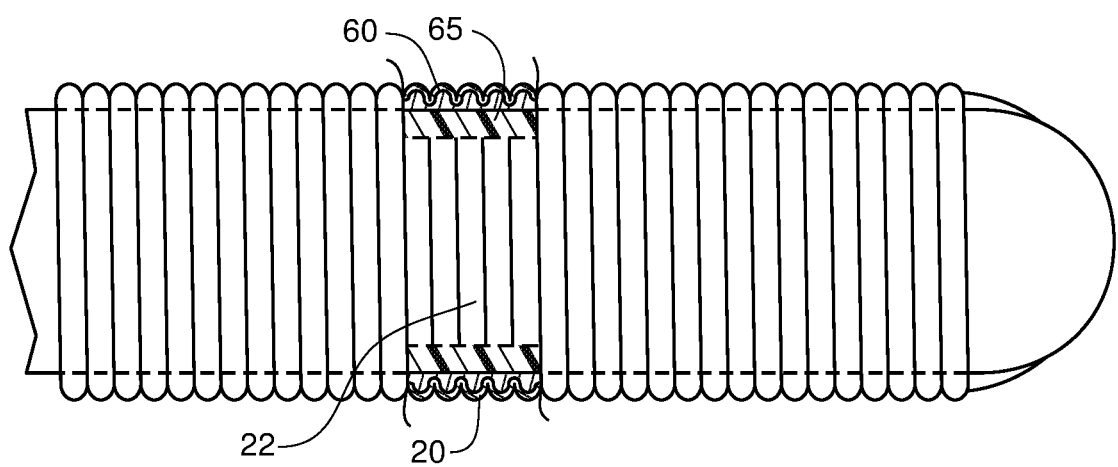
FIG. 14 is a partial cut-away perspective view of a helical assembly showing an embodiment of a corrugated surface element overlying the core element.

With reference to FIGS. 13A-13C, and as previously mentioned, helical prosthesis 10 can include a surface element 60 applied to or formed integrally with the outer surface of core element 50 and configured to impart a specialized protective interface against gastric fluids. Surface element 60 can also increase the lifespan of helical prosthesis 10 beyond the typical 6-12 month life span of conventional intragastric balloons.

Additionally, core element 50 can have on at least a part of its surface a hydrophilic surface layer in order to produce a low-friction surface character of helical prosthesis 10 by treatment with a liquid swelling medium. In one embodiment, helical prosthesis 10 is provided in a package comprising a gas impermeable material to accommodate the liquid swelling medium already prepared for straightening and direct insertion into a delivery device (discussed in more detail below), and, thereafter frictionless deployment into the gastric cavity in a substantially sterile condition.

In another embodiment, core element 50 includes a nonwoven porous surface element affixed to or incorporated on its outer surface. The surface element can be manufactured by an electrospinning process to deposit biocompatible polymer fibers on the smooth surface of core element 50, which promotes deposition of a protective mucous layer from the stomach wall therein.

Core element 50 and surface element 60 can comprise a silicone material, silicone copolymer, polyurethane polymer material, or any other polymer material that is resistant to deterioration by gastric juices.

Various balloon shell materials can be used in embodiments. For example, one inflatable intragastric balloon material is commercially available as the ORBERA System from Allergan Medical of Irvine, Calif. The shell material of the ORBERA balloon is a 2-component high-temperature vulcanizing phenyl silicone with a platinum catalyzed curing system. Such a material has been proven suitable for implant duration of up to 6 months. U.S. Patent Publication No. 2014/0066968 (incorporated herein by reference in its entirety) discloses an intragastric balloon with a 12-month life span. The intragastric balloon has a shell made of a material with as good as or better than initial mechanical properties of previous materials; i.e. higher ultimate tensile strength and elongation at break, lower stiffness, higher acid stability, and improved resistance to infection.

Embodiments of helical prosthesis 10 can incorporate various suitable materials that are commercially available on the market, as appreciated by those of skill in the art. Moreover, embodiments provide an alternative approach to conventional solutions in that the balloon membrane of helical balloon element 40 is substantially insulated from contact with the gastric juices. More specifically, core element 50 and an overlying surface element 60 are primarily responsible for providing acid stability, a lubricious surface, and antimicrobial functions.

Conventional balloons are known to become more stiff and fragile in response to the gastric acidic environment. Since these balloons are typically spherical or pear-shaped and are required to expand to a volume of 200-500 ml or more, the balloon wall is placed under contrasting demands of flexibility, stretchability, durability, crack resistance, longevity, acid resistance, and microbial resistance. Accordingly, conventional balloons tend to be bulky, requiring placement gastroscopically rather than via an orogastric tube. Removing such balloons requires deflation by puncturing with a gastroscopic instrument and either aspirating the contents of the balloon and removing it, or allowing the fluid to pass into the patient's stomach.

In one embodiment of helical prosthesis 10, at least one of core element 50 or surface element 60 includes an impregnated PTFE layer forming protection and other favorable surface function to the underlying silicone layer of the core element from the strongly acidic gastric fluid, thereby providing maximum durability and long-term usability in the stomach.

Variants of core element 50 or helical prosthesis 10 are also envisioned. In one embodiment, an ePTFE ribbon or tape wrap can be wrapped helically around core element 50 into a tubular shape under tension. In another embodiment, a polymeric layer can be applied to core element 50 from a solution; i.e., the polymer can be dissolved in a solvent, and upon evaporation of the solvent the polymer can be deposited on core element 50 and penetrate into the pores of the ePTFE layer. It is therefore an advantage of embodiments of helical prosthesis 10 to provide an ePTFE covering of an intragastric expandable helical prosthesis having enhanced longitudinal elongation and radial expansion properties. It is also an advantage to provide an ePTFE polymer core combination in which the ePTFE covering has the ability to expand and contract in unison with polymeric core element 50.

One potential drawback in utilizing a thick layer of ePTFE material is that it is relatively radially non-compliant, however, those skilled in the art are aware of recent technologies of ePTFE application that render ePTFE relatively semi-compliant.

Advantageously, the surface element described herein can provide significantly reduced silicone cracks in an otherwise uncovered core element that may occur due to uneven curing of the silicone during the processing of the core element. The surface element of the present disclosure can provide a porous outer layer to permit a lubricious surface apposed to the gastric mucosa. Mucus, synthesized and released from epithelial cells, adheres to the mucosal surface as a thin continuous gel layer.

There is good evidence that the adherent mucus along the inner gastric wall plays an important role in the protection of gastro-duodenal mucosa from the indigenous effects of acid and pepsin. Adherent mucus provides a stable layer which supports surface neutralization of acid by mucosal bicarbonate output and acts as a permeability barrier to luminal pepsin. The adherent mucus layer is continuous.

Figure 15:
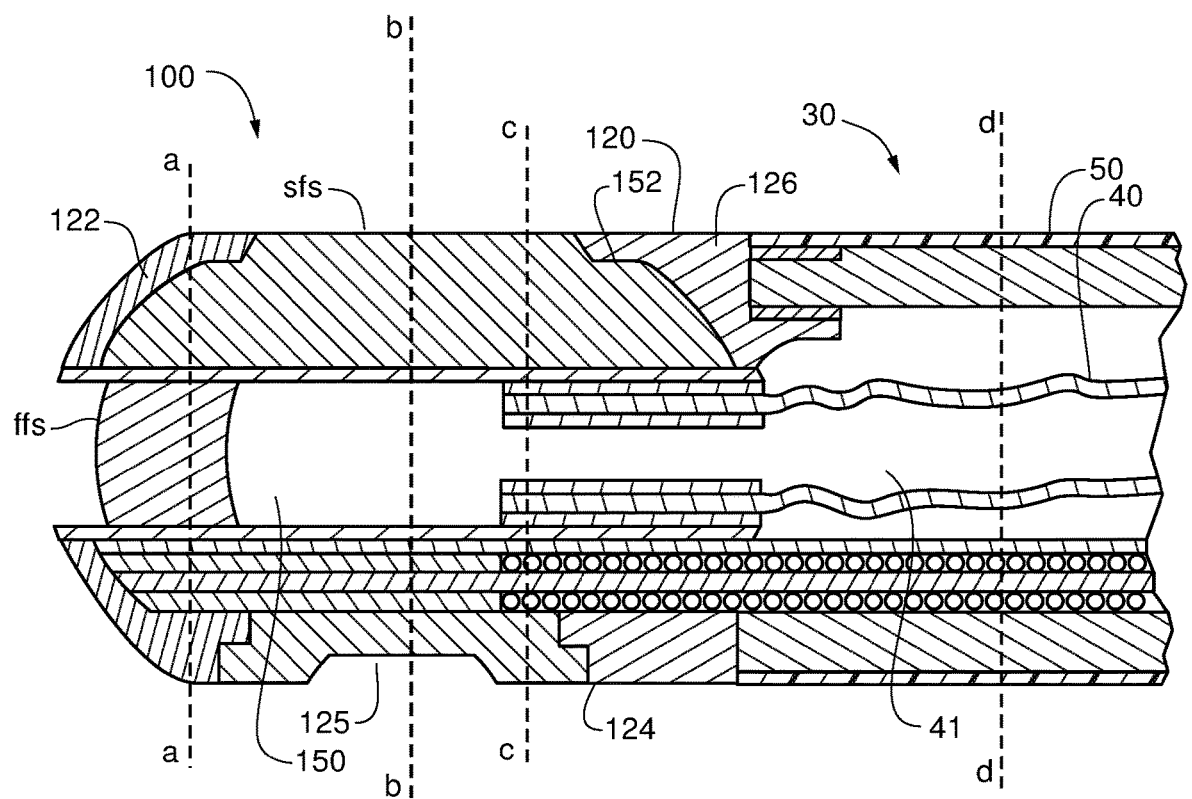
FIG. 15 is a side sectional view of a proximal end fitting coupled to the proximal portion of a helical assembly according to one embodiment.

Turning to FIG. 15, proximal end fitting 25 of helical prosthesis 10 is a versatile fluid access apparatus and mounting region. Proximal end fitting 25 includes a housing 120 having a side-facing self-sealing septum SFS and a front-facing self-sealing septum FFS enclosed therein.

In various embodiments and uses, these elements may be oriented in ways that are not necessarily "side-facing" or "front-facing," and these terms are used herein for convenience and with reference to the orientation of the drawings, without limitation. Housing 120 includes a reservoir 150 and mounting regions for helical balloon element 40 and helical spring element 35.

The septums SFS and FFS are elastomeric and received in sealing relation to two orthogonal openings in housing 120 so that the septums SFS and FFS cooperate to define fluid reservoir 150 in the center of housing 120, wherein reservoir 150 is generally cylindrical and concentric with septum FFS. Septums SFS and FFS are pierceable by injection needles to gain fluid access to reservoir 150. In turn, fluid reservoir 150 is in free fluid communication with lumen 41 of helical balloon element 40 through fluid conduit 152. Further, housing portion 120 provides helical balloon element 40, helical spring element 35 and core element 50/surface element 60 secure attachment to proximal end fitting 25. Thus, proximal end fitting 25 allows front-facing and side-facing access to an internal reservoir that is in fluid communication with helical balloon element 40 in helical prosthesis 10. Proximal end fitting 25 further provides secure support to helical spring element 35.

Figure 16:
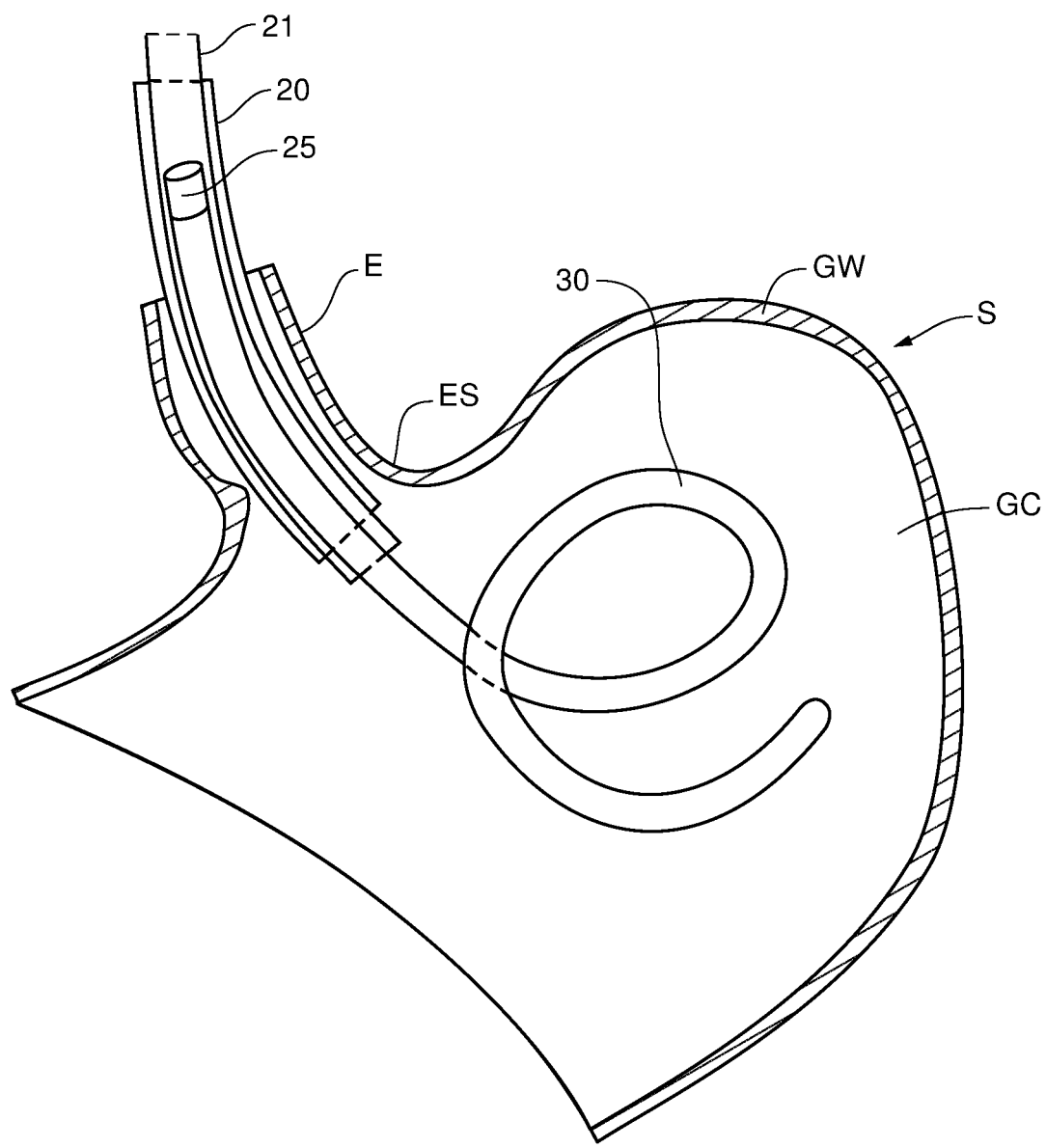
FIG. 16 is a sectional view of the distal esophagus and proximal stomach with a helical prosthesis partially deployed into the gastric cavity.
Figure 17:
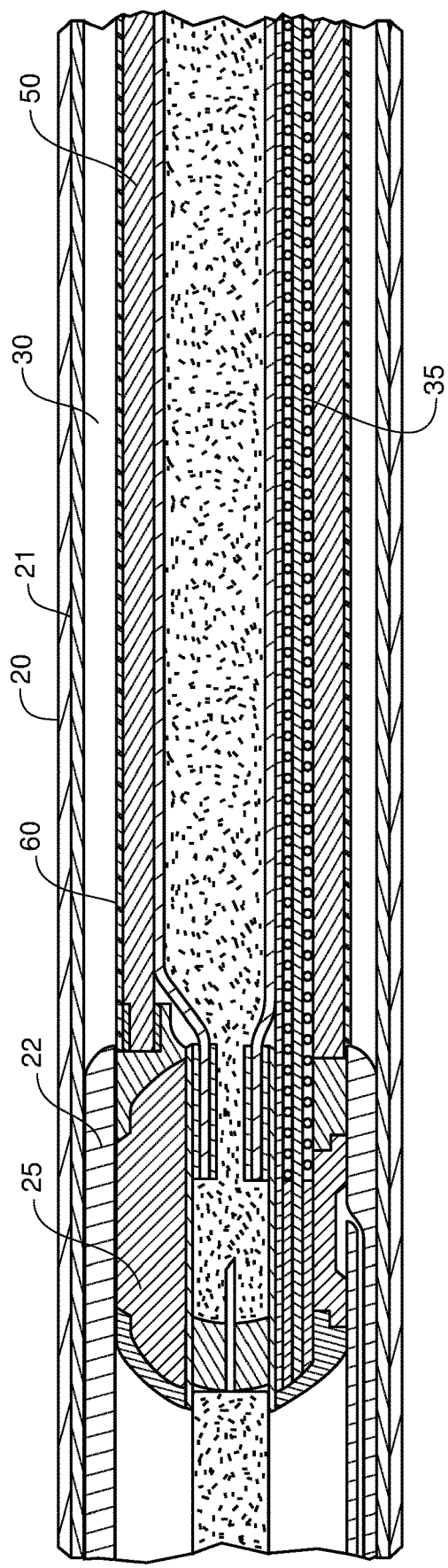
FIG. 17 is a side cross-sectional view of a proximal portion of a helical prosthesis including a proximal end fitting coupled to a helical assembly, straightened and loaded within the lumen of a delivery tube which in turn is disposed within the lumen of an orogastric tube.

FIG. 16 depicts a stage of delivery of helical prosthesis 10 to a stomach S. Referring also to FIG. 17, helical prosthesis 10 is straightened and loaded within a lumen of a delivery tube 21, which is concentrically disposed within a lumen of an orogastric tube 20. A guiding catheter 22 is removably coupled to proximal end fitting 25, which, in turn, is securely coupled to helical prosthesis 10. The distal portion of orogastric tube 20 is passed down the esophagus E and through the esophageal sphincter ES, into the stomach S. Delivery tube 21 is slidably disposed within the lumen of orogastric tube 20 and protrudes out at a distal tip of orogastric tube 20. Helical prosthesis 10, loaded as described above within the lumen of delivery tube 21, is shown in FIG. 16 in the process of being delivered and deployed into the gastric cavity GC. During delivery, helical balloon element 40 of helical prosthesis 10 is deflated and stretched or otherwise arranged into a linear configuration as shown in FIG. 17, in order to be loaded into the lumen of delivery tube 21.

During expulsion from the distal end of delivery tube 21, helical prosthesis 10 coils spontaneously and assumes a reposed configuration due to the biasing action provided by helical spring element 35 therein. Simultaneously, or thereafter, a fluid such as saline and/or contrast material is injected through a fill tube (not shown) into proximal end fitting 25 to inflate helical balloon element 40. Inflation of helical balloon element 40 is accompanied by widening of the radii of curvature of convolutions 45 and overall expansion of helical prosthesis 10. In one embodiment, the procedure is performed under fluoroscopic guidance. Once inflated, the fill tube and orogastric tube 20 are removed.

Embodiments of helical prosthesis 10 provide numerous advantages over conventional intragastic balloons and other devices. For example, upon delivery and deployment helical prosthesis 10 can spontaneously expand within a user's stomach such that manual expansion or adjustment may not be necessary. Helical prosthesis 10 is versatile, however, and can provide for further expansion or adjustment, at initial deployment or later, if desired by a physician.

The helical shape and structure of helical prosthesis 10 provides numerous advantages, including that the "pigtail"-like structure provides gastric delay, which can increase a user's satiety. Additionally, the overall helical shape enables food and gastric materials to pass through the center of helical prosthesis 10. The helical shape also reduces contact of helical prosthesis 10 with the gastric wall of the stomach, and natural movement of helical prosthesis 10 within the stomach means that it is not always in contact with the same part of the gastric wall. This is easier on the mucosa than larger, more solid, non-helical devices. The movement of helical prosthesis 10 within the stomach also reduces pressure from the weight of the device such that pressure sores may be reduced or avoided.

Still other advantages will be apparent to those having skill in the art.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

What is claimed is:

1. An intragastric helical prosthesis for transoral placement into a user's stomach to treat obesity, the helical prosthesis comprising:
    a helical assembly comprising;
        a tubular elastomeric core element defining a first lumen and a second lumen;
        a helical balloon element disposed in the first lumen; and a helical spring element disposed in the second lumen; and a proximal end fitting having a housing, the proximal end fitting coupled to:
the core element,
the helical balloon element, and
the helical spring element,
wherein the housing includes:
a central reservoir in fluid communication with the helical balloon element, and
at least two septums, wherein the at least two septums provide fluid access to the central reservoir.

2. The helical prosthesis according to claim 1, wherein the core element has proximal and distal ends, and wherein at least one of the first or second lumens is a central passageway extending axially through the core element.

3. The helical prosthesis according to claim 1, wherein the core element comprises a silicone elastomer.

4. The helical prosthesis according to claim 1, wherein the core element is a helical medical tubing and at least one characteristic of the tubing is variable along a length extending from a proximal end to a terminal end.

5. The helical prosthesis according to claim 1, wherein the core element has variable flexibility along a length from a proximal end to a terminal end.

6. The helical prosthesis according to claim 1, wherein the helical assembly has convolutions of variable radii of curvature along its length.

7. The helical prosthesis of claim 1, wherein the helical balloon element has an inflatable volume of approximately 100-300 cc.

8. The helical prosthesis according to claim 1, wherein the helical balloon element and the helical spring element are unattached to the core element, and are free to move independently during winding and unwinding of the helical assembly.

9. The helical prosthesis of claim 1, wherein the helical balloon element includes an elongated cylindrical balloon membrane.

10. The helical prosthesis of claim 9, wherein the elongated cylindrical balloon membrane is compliant or semi-compliant.

11. The helical prosthesis of claim 1, wherein the helical balloon element includes a fiber supporting structure applied loosely over a length of an elongated cylindrical balloon membrane, whereby inflation of the elongated cylindrical balloon membrane reconfigures the fiber supporting structure to urge the helical assembly into a predetermined helical configuration.

12. The helical prosthesis of claim 11, wherein the fiber supporting structure and the elongated cylindrical balloon membrane are separate and unattached, to maintain flexibility when inflated.

13. The helical prosthesis of claim 11, wherein the fiber supporting structure includes a proximal portion arranged such that the proximal portion and the elongated cylindrical balloon membrane are securely attached to a mounting region of the proximal end fitting.

14. The helical prosthesis according to claim 11, wherein the fiber supporting structure includes a spring formed of a super elastic shape-memory alloy.

15. The helical prosthesis of claim 1, wherein the helical balloon element exhibits around 30% increase in mean straightening force when inflated across the working pressure range while the helical assembly is in a helical configuration.

16. The helical prosthesis according to claim 15, wherein the helical spring element includes a fiber-reinforced composite spring.

17. The helical prosthesis of claim 1, wherein the helical spring element comprises a flexible tubing with a helical spring wire in its lumen.

18. The helical prosthesis of claim 1, wherein the helical balloon element and the helical spring element are coupled to the proximal end fitting but not directly coupled to one another.

19. The helical prosthesis of claim 1, wherein the helical assembly takes the form of a helically shaped spring of a predetermined length and pitch provided with first and second ends and means for expanding the spring from a first state of a certain diameter to a second state of a larger diameter, and from a first state of a certain diameter to a second state of a smaller diameter.

20. The helical prosthesis of claim 1, wherein a plurality of convolutions cooperatively act as a flexible spring permitting dynamic engagement of the stomach wall at spaced locations, for minimizing complications due to constant pressure trauma against the stomach wall.

21. The helical prosthesis of claim 20, wherein the convolutions define a central opening extending therethrough.

22. The helical prosthesis of claim 21, wherein the central opening is configured to slow down gastric emptying.

23. The helical prosthesis of claim 20, wherein the convolutions comprise a pig-tail distal region for preventing migration of the prosthesis out of a pylorus.

24. The helical prosthesis of claim 1, wherein the proximal end fitting includes the housing wherein one of the at least two septums is a front-facing elastomeric septum being penetrable by an inflation needle to gain access to the central fluid reservoir.

25. The helical prosthesis of claim 1, wherein the proximal end fitting includes means to allow capturing of the prosthesis to facilitate removal thereof from the stomach.

26. The helical prosthesis of claim 1, wherein the proximal end fitting includes means for allowing inflation/deflation of the helical assembly.

27. The helical prosthesis of claim 1, wherein the proximal end fitting includes the housing wherein one of the at least two septums is a side-facing elastomeric septum being penetrable by an inflation needle to gain access to the central reservoir.

28. The helical prosthesis of claim 27, wherein the proximal end fitting includes the housing having an annular external groove configured to engage a snare wire loop extending from a guiding catheter introduced transorally, the snare loop configured to capture and fix the proximal end fitting in position to allow inflation needle penetration of the side-facing elastomeric septum to gain access to the central reservoir.

* * * * *